United States Patent
DeLucas et al.

(10) Patent No.: US 7,214,540 B2
(45) Date of Patent: *May 8, 2007

(54) METHOD FOR SCREENING CRYSTALLIZATION CONDITIONS IN SOLUTION CRYSTAL GROWTH

(75) Inventors: Lawrence J. DeLucas, Birmingham, AL (US); Terry L. Bray, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 201 days.

This patent is subject to a terminal disclaimer.

(21) Appl. No.: 09/947,665

(22) Filed: Sep. 6, 2001

(65) Prior Publication Data

US 2003/0096421 A1    May 22, 2003

Related U.S. Application Data

(63) Continuation-in-part of application No. 09/543,326, filed on Apr. 5, 2000, now abandoned.

(60) Provisional application No. 60/128,018, filed on Apr. 6, 1999.

(51) Int. Cl.
*G01N 33/00* (2006.01)

(52) U.S. Cl. .................... 436/86; 436/174

(58) Field of Classification Search ............. 436/86, 436/174
See application file for complete search history.

(56) References Cited

U.S. PATENT DOCUMENTS

| | | | |
|---|---|---|---|
| 3,570,515 A | 3/1971 | Kinner | |
| 3,747,628 A | 7/1973 | Holster et al. | |
| 4,046,159 A | 9/1977 | Pegourie | |
| 4,119,368 A | 10/1978 | Yamazaki | |
| 4,153,855 A | 5/1979 | Feingold | |
| 4,245,673 A | 1/1981 | Bouteille et al. | |
| 4,263,010 A | 4/1981 | Randolph | |

(Continued)

FOREIGN PATENT DOCUMENTS

AU    779792    8/2005

(Continued)

OTHER PUBLICATIONS

"BMST Pervasive Technologies Concept Paper, BMST Initiative Thrust Area: Emerging of Breakthrough Process Technologies Definition of the Thrust Area NACFAM," printed from http://www.nacfam.org/bmstlbmstemergingtechnologies.html on Feb. 26, 2002 (5 pages).

(Continued)

*Primary Examiner*—Monique T. Cole
(74) *Attorney, Agent, or Firm*—Bingham McCutchen LLP

(57) ABSTRACT

A method of screening protein crystal growth conditions on a nano or meso scale comprises providing a micro-electromechanical chip with a plurality of micro-chambers in the micro-electromechanical chip. A protein solution is placed into the micro-chambers by an automated jet type dispensing means with nano or meso scale precision. The protein crystal growth conditions of each of the micro-chambers is adjusted so that the protein crystal growth conditions of each of the micro-chambers differs. Crystallization of the protein solution in the micro-chambers is effected. Protein crystal growth in the micro-chambers is then observed.

16 Claims, 3 Drawing Sheets

U.S. PATENT DOCUMENTS

| | | |
|---|---|---|
| 4,434,704 A | 3/1984 | Surjaatmadja |
| 4,517,048 A | 5/1985 | Shlichta |
| 4,668,584 A | 5/1987 | Uzgiris et al. |
| 4,755,363 A | 7/1988 | Fujita et al. |
| 4,833,233 A | 5/1989 | Carter |
| 4,886,646 A | 12/1989 | Carter et al. |
| 4,898,582 A | 2/1990 | Faste |
| 4,900,147 A | 2/1990 | Bowley et al. |
| 4,909,933 A | 3/1990 | Carter et al. |
| 4,919,899 A | 4/1990 | Herrmann et al. |
| 4,948,564 A | 8/1990 | Root et al. |
| 5,009,861 A | 4/1991 | Plaas-Link |
| 5,013,531 A | 5/1991 | Snyder et al. |
| 5,076,698 A | 12/1991 | Smith et al. |
| 5,078,975 A | 1/1992 | Rhodes et al. |
| 5,085,562 A | 2/1992 | Van Lintel |
| 5,088,515 A | 2/1992 | Kamen |
| 5,096,388 A | 3/1992 | Weinberg |
| 5,096,676 A | 3/1992 | McPherson et al. |
| 5,106,592 A | 4/1992 | Stapelmann et al. |
| 5,124,935 A | 6/1992 | Wallner et al. |
| 5,126,115 A | 6/1992 | Fujita et al. |
| 5,130,105 A | 7/1992 | Carter et al. |
| 5,164,558 A | 11/1992 | Huff et al. |
| 5,171,132 A | 12/1992 | Miyazaki et al. |
| 5,193,685 A | 3/1993 | Trevithick |
| 5,221,410 A | 6/1993 | Kushner et al. |
| 5,224,843 A | 7/1993 | Van Lintel |
| 5,256,241 A | 10/1993 | Noever |
| 5,259,737 A | 11/1993 | Kamisuki et al. |
| 5,265,327 A | 11/1993 | Faris et al. |
| 5,290,240 A | 3/1994 | Horres, Jr. |
| 5,336,062 A | 8/1994 | Richter |
| 5,346,372 A | 9/1994 | Naruse et al. |
| 5,362,325 A | 11/1994 | Shiraishi et al. |
| 5,375,979 A | 12/1994 | Trah |
| 5,376,252 A | 12/1994 | Ekstrom et al. |
| 5,400,741 A | 3/1995 | DeTitta et al. |
| 5,419,278 A | 5/1995 | Carter |
| 5,423,287 A | 6/1995 | Usami et al. |
| 5,529,465 A | 6/1996 | Zengerle et al. |
| 5,531,185 A | 7/1996 | Asano et al. |
| 5,544,254 A | 8/1996 | Hartley et al. |
| 5,581,476 A | 12/1996 | Osslund |
| 5,593,130 A | 1/1997 | Hansson et al. |
| 5,637,469 A | 6/1997 | Wilding et al. |
| 5,641,681 A | 6/1997 | Carter |
| 5,642,015 A | 6/1997 | Whitehead et al. |
| 5,643,540 A | 7/1997 | Carter et al. |
| 5,659,171 A | 8/1997 | Young et al. |
| 5,660,370 A | 8/1997 | Webster |
| 5,681,024 A | 10/1997 | Lisec et al. |
| 5,705,018 A | 1/1998 | Hartley |
| 5,716,852 A | 2/1998 | Yager et al. |
| 5,726,404 A | 3/1998 | Brody et al. |
| 5,728,559 A | 3/1998 | Nilsson et al. |
| 5,759,014 A | 6/1998 | Van Lintel |
| 5,775,371 A | 7/1998 | Pan et al. |
| 5,790,421 A | 8/1998 | Osslund |
| 5,836,750 A | 11/1998 | Cabuz |
| 5,842,787 A | 12/1998 | Kopf-Sill et al. |
| 5,855,753 A | 1/1999 | Trau et al. |
| 5,869,604 A | 2/1999 | Rousseau et al. |
| 5,872,010 A | 2/1999 | Karger et al. |
| 5,873,394 A | 2/1999 | Meltzer |
| 5,875,817 A | 3/1999 | Carter |
| 5,876,187 A | 3/1999 | Forster et al. |
| 5,876,675 A | 3/1999 | Kennedy |
| 5,885,470 A | 3/1999 | Parce et al. |
| 5,922,210 A | 7/1999 | Brody et al. |
| 5,932,100 A | 8/1999 | Yager et al. |
| 5,932,799 A | 8/1999 | Moles |
| 5,942,443 A | 8/1999 | Parce et al. |
| 5,948,684 A | 9/1999 | Weigl et al. |
| 5,958,694 A | 9/1999 | Nikiforov |
| 5,961,934 A | 10/1999 | Arnowitz et al. |
| 5,964,995 A | 10/1999 | Nikiforov et al. |
| 5,971,158 A | 10/1999 | Yager et al. |
| 5,973,779 A | 10/1999 | Ansari et al. |
| 5,974,867 A | 11/1999 | Forster et al. |
| 5,985,356 A | 11/1999 | Schultz et al. |
| 5,997,636 A | 12/1999 | Gamarnik et al. |
| 6,007,309 A | 12/1999 | Hartley |
| 6,007,775 A | 12/1999 | Yager et al. |
| 6,031,082 A | 2/2000 | Nielsson et al. |
| 6,034,804 A | 3/2000 | Bashkansky et al. |
| 6,036,920 A | 3/2000 | Pantoliano et al. |
| 6,039,804 A | 3/2000 | Kim et al. |
| 6,043,080 A | 3/2000 | Lipshutz et al. |
| 6,057,159 A | 5/2000 | Lepre |
| 6,069,934 A | 5/2000 | Verman et al. |
| 6,110,273 A | 8/2000 | Sanjoh |
| 6,110,986 A | 8/2000 | Nozawa et al. |
| 6,117,232 A | 9/2000 | Sanjoh |
| 6,123,769 A | 9/2000 | Sanjoh |
| 6,129,826 A | 10/2000 | Nikiforov et al. |
| 6,134,950 A | 10/2000 | Forster et al. |
| 6,136,272 A | 10/2000 | Weigl et al. |
| 6,143,248 A | 11/2000 | Kellogg et al. |
| 6,155,282 A | 12/2000 | Zachary et al. |
| 6,156,181 A | 12/2000 | Parce et al. |
| 6,171,865 B1 | 1/2001 | Weigl et al. |
| 6,174,365 B1 | 1/2001 | Sanjoh |
| 6,174,675 B1 | 1/2001 | Chow et al. |
| 6,186,660 B1 | 2/2001 | Kopf-Sill et al. |
| 6,235,175 B1 | 5/2001 | Dubrow et al. |
| 6,238,538 B1 | 5/2001 | Parce et al. |
| 6,258,331 B1 * | 7/2001 | Sanjoh .................... 422/245.1 |
| 6,268,158 B1 | 7/2001 | Pantoliano et al. |
| 6,291,192 B1 | 9/2001 | Pantoliano et al. |
| 6,296,673 B1 * | 10/2001 | Santarsiero et al. ...... 23/295 R |
| 6,296,811 B1 | 10/2001 | Sasaki |
| 6,297,021 B1 | 10/2001 | Nienaber et al. |
| 6,303,322 B1 | 10/2001 | Pantoliano et al. |
| 6,319,315 B1 | 11/2001 | Sanjoh |
| 6,368,402 B2 | 4/2002 | DeTitta et al. |
| 6,387,273 B1 | 5/2002 | Abedi |
| 6,402,837 B1 | 6/2002 | Shtrahman et al. |
| 6,404,849 B1 | 6/2002 | Olson et al. |
| 6,406,903 B2 | 6/2002 | Bray et al. |
| 6,409,832 B2 | 6/2002 | Weigl et al. |
| 6,413,778 B1 | 7/2002 | Carpenter et al. |
| 6,417,007 B1 | 7/2002 | Gittleman et al. |
| 6,423,536 B1 | 7/2002 | Jovanovich et al. |
| 6,454,945 B1 | 9/2002 | Weigl et al. |
| 6,468,346 B2 | 10/2002 | Arnowitz et al. |
| 6,488,896 B2 | 12/2002 | Weigl et al. |
| 6,630,006 B2 | 10/2003 | Santarsiero |
| 6,742,661 B1 | 6/2004 | Schulte et al. |
| 6,743,399 B1 | 6/2004 | Weigl et al. |
| 2001/0016191 A1 | 8/2001 | Osslund |
| 2001/0016314 A1 | 8/2001 | Anderson et al. |
| 2001/0019845 A1 | 9/2001 | Bienert et al. |
| 2001/0027745 A1 | 10/2001 | Weigl et al. |
| 2001/0032582 A1 | 10/2001 | DeTitta et al. |
| 2001/0055669 A1 | 12/2001 | Schultz et al. |
| 2001/0055775 A1 | 12/2001 | Schultz et al. |
| 2002/0022250 A1 | 2/2002 | Hendrickson et al. |
| 2002/0029814 A1 | 3/2002 | Unger et al. |
| 2002/0048610 A1 | 4/2002 | Cima et al. |
| 2002/0054663 A1 | 5/2002 | Olson et al. |
| 2002/0062783 A1 | 5/2002 | Bray |
| 2002/0064485 A1 | 5/2002 | Delucas et al. |
| 2002/0067800 A1 | 6/2002 | Newman et al. |

| | | | |
|---|---|---|---|
| 2002/0164812 A1 | 11/2002 | DeLucas et al. | |
| 2003/0022383 A1 | 1/2003 | DeLucas | |
| 2003/0022384 A1 | 1/2003 | DeLucas et al. | |
| 2003/0027348 A1 | 2/2003 | DeLucas et al. | |
| 2003/0096421 A1 | 5/2003 | DeLucas et al. | |
| 2003/0180960 A1 | 9/2003 | Consenza et al. | |

FOREIGN PATENT DOCUMENTS

| | | | |
|---|---|---|---|
| DE | 19631395 A | | 5/1998 |
| EP | 0 553 539 A1 | | 8/1993 |
| EP | 592 094 | | 4/1994 |
| EP | 703 384 | | 3/1996 |
| EP | 779 438 | | 6/1997 |
| EP | 0 815 940 A2 | | 1/1998 |
| EP | 829 380 | | 3/1998 |
| EP | 706 004 | | 4/1998 |
| EP | 845 603 | | 8/1998 |
| EP | 999 055 | | 10/2000 |
| GB | 2 155 152 | | 9/1985 |
| GB | 2 308 480 | | 6/1997 |
| JP | 02001013054A A1 | | 1/2001 |
| NZ | 514732 | | 1/2004 |
| WO | WO 98/07069 | | 2/1998 |
| WO | WO 99/00655 | | 1/1999 |
| WO | WO 99/04361 | | 1/1999 |
| WO | WO 99/17093 | | 4/1999 |
| WO | WO 99/23284 | | 5/1999 |
| WO | WO 99/52633 | | 10/1999 |
| WO | WO 00/00678 | | 1/2000 |
| WO | WO 00/43748 | | 7/2000 |
| WO | WO 00/60345 | | 10/2000 |
| WO | WO 00/60345 A1 | | 10/2000 |
| WO | WO 00/78445 | | 12/2000 |
| WO | WO 01/09585 | | 2/2001 |
| WO | WO 01/26797 A2 | | 4/2001 |
| WO | WO 01/92293 A2 | | 12/2001 |
| WO | WO 03/012430 | | 2/2003 |

OTHER PUBLICATIONS

"Hampton Research Solutions for Crystal Growth," printed from http://www.hamptonresearch.com on Feb. 22, 2001 (2 pages).

"High throughput protein crystallization — EMBL Practical Course on Protein Expression, Purification and Crystallization — Aug. 14th-20th, 2000 EMBL Outstation Hamburg, Germany," printed from http://www.structure.llnt.gov/Xray/tutorial/HighjhroughpuLEMBL_full.html on Apr. 12, 2002 (10 pages).

Mochalkin et al. "High-Throughput Structure Determination in an Informatics Environment," (2001) printed from http://www.accetrys.com/ webzine on Aug. 1, 2002 (4 pages).

"Meeting Summaries," printed from http://www.-nmr.cabm.rutgers.edu/labdocuments/mtgsummaries/mtgsummaries.html on Apr. 12, 2002 (32 pages).

"Minutes May 1-2, 2001 Biological and Environmental Research Advisory Committee (BERAC)," printed from http://www.er.doe.gov/production/ober/berac/5-01 mins.html on Apr. 12, 2002 (10 pages).

"NIGMS—Advisory Council Meeting Minutes, 5-98 Minutes of the National Advisory General Medical Sciences Council—May 14-15, 1998," printed from http://www.nigms.nih.gov/about_nigms/council_may98.html on Apr. 12, 2002 (10 pages) (site last updated Jul. 17, 1998).

"NIGMS—NIGMS Structural Genomics Targets Workshop Feb. 11-12, 1999" printed from http://www.nigms.nih.gov/news/meetings/structural_genomics.jargets.html on Apr. 12, 2002 (18 pages).

"NIGMS Protein Structure Initiative Meeting Summary Apr. 24, 1998," printed from http://www.nigms.nih.gov/news/reports/protein,.structure.html on Apr. 12, 2002 (12 pages) (site last updated Jun. 2, 1998).

Advertisement: "The first Fully Automated Digital Imaging System specifically for crystallographers — Crystal Score, Cyber Lab," ACA Newsletter 1:28 (Spring, 2000).

Andersen, G.R. et al., "A Spreadsheet Approach to Automated Protein Crystallization," *J. Appl. Cryst.*, E 1996, pp. 236-240, vol. 29, International Union of Crystallography, Great Britain.

Arkin, A., "Stochastic Logic in Biochemical and Genetic Reaction Networks: Theory and Experiment With Application to Bacterial Pathogenesis," Physical Biosciences Division, 1998.

Baird, J.K., "Theory of protein crystal nucleation and growth controlled by solvent evaporation," *J. Cryst. Growth* 204: 553-562 (1999).

Baldock, P. et al., "A comparison of microbatch and vapour diffusion for initial screening of crystallization conditions," *J. Cryst. Growth* 168: 170-174 (1996).

Beckmann, W. et al., The Effect of Additives on Nucleation: A Low Cost Automated Apparatus, *J. Crystal Growth* 99:1061-1064 (1990).

Berger, I. et al., "A Highly Efficient 24-Condition Matrix for the Crystallization of Nucleic Acid Fragments," —Acta Cryst., 1996, pp. 465-468, Section D, International Union of Crystallography, Great Britain.

Berry, MB., "Protein Crystallization: Theory and Practice," excerpts from "Structure and Dynamics of E. coli Adenylate Kinase," by Michael B. Berry (Sep. 17, 1995), 12 pages, printed from http://www.bioc.nce.edu/~berry/crystallization/crystallization.

Blow, D.M. et al., "Control of nucleation of protein crystals," *Protein Sci.* 3:1638-1643 (1994).

Brochure: Automatic Protein Crystallization System. Douglas Instruments Limited (1990)(4 pages).

Brodersen, D.E. et al., "Computer Programs XAcr. a program for construction, automated setup and bookkeeping of crystallization experiments," *J. Appl. Cryst.* 32:1012-1016 (1999).

Bullock, E. et al., "Apparatus for the growth of crystals from small vols. of solutions," *J. Physics E: Sci. Instrum.* 5:4 12-413 (1972).

Burley, S. K. of al., "Structural genomics: beyond the Human Genome Project," *Nat. Genet.* 23:151-157 (1999).

Carter, C.W. Jr., "Response Surface Methods for Optimizing and Improving Reproducibility of Crystal 7 Growth," Methods in Enzymology, 1997, pp. 74-99, vol. 276, Academic Press, Inc.

Carter, C. W., "Efficient Factorial Designs and the Analysis of Macromolecular Crystal Growth Conditions," *Methods: A Companion to Meth. Enzymol.* 1(1): 12-24 (1990).

Casay, G.A. of al., "Laser scattering in a hanging drop vapor diffusion apparatus for protein crystal growth in a microgravity environment," *J. Crystal Growth* 122:95-1 01 (1992).

Catalog, 63 pp. Hampton Research Corporation (copyright 1999).

Chayen, N.E. et al., Purification, crystallization and initial X-ray analysis of the $C_1$ subunit of the astaxanthin protein, $V_{600}$, c the chondrophore *Velella velella*, Acta Cryst. D55:266-268 (1999).

Chayen, N. E. et al., "An Automated System for Micro-Batch Protein Crystallization and Screening," *J. Appl. Cryst.* 23:297-302 (1990).

Chayen, N. E. et al., "Apocrustacyanin Al from the lobster carotenoprotein a-crustacyanin: crystallization and initial X-ray analysis involving softer X-rays," Acta Cryst. D56:1 064-1066 (Aug. 2000).

Chayen, N. E. et al., "Control of nucleation in the crystallization of lysozyme," *Protein Sci.* 2:113-118 (1993).

Chayen, N. E. et al., "Crystallization and initial X-ray analysis of β3-crustacyanin, the dimmer of apoproteins E A2 and C1, each with a bound astaxanthin molecule," Acta Cryst., 1996, pp. 409-41 0, Section D52, — International Union of Crystallography, Great Britain.

Chayen, N. E. et al., "Crystallization and Initial X-ray analysis of xylose isomerase from Thermotoga neapolitana," Acta. Cryst., 1997, pp. 229-230, Section D53, International Union of Crystallography, Great — Britain.

Chayen, N. E. et al., "Is lysozyme really the ideal model protein?," Journal of Crystal Growth, 2001, pp. 7 262-264, vol. 232, Elsevier Science B.V., The Netherlands.

Chayen, N. E. et al., "Microbatch crystallization under oil — a new technique allowing many small-vol crystallization trials," *J. Crystal Growth* 122: 176-1 80 (1992).

Chayen, N. E. et al., "New developments of the IMPAX small-volume automated crystallization system" Acta Cryst. D50:456-458 (1994).
Chayen, N. E. et al., "Porous Silicon: an Effective Nucleation-Inducing Material for Protein Crystallization" J. Mol. Biol. 312:591-595 (2001).
Chayen, N. E. et al., "Protein crystallization for genomics: towards high-throughput optimization techniques" Acta Cryst. D58:921-927 (2002).
Chayen, N. E. et al., "Solubility-of glucose isomerase in ammonium sulphate solutions," Journal of Crystal Growth, 1988, pp. 112-116, vol. 90, Elsevier Science B.V., The Netherlands.
Chayen, N. E. et al., "Space-grown crystals may prove their worth," Nature 398(6722):20 (1999).
Chayen, N. E. et al., "Trends and Challenges in Experimental Macromolecular Crystallography," Quart. Rev. Biophysics 29(3):227-278 (Aug. 1996).
Chayen, N. E. et al., "Trigonal crystals of glucose isomerase require thymol for their growth and stability," — Journal of Crystal Growth, 1989, pp. 367-374, vol. 97, Elsevier Science B.V., The Netherlands.
Chayen, N. E. et al., "A novel technique to control the rate of vapour diffusion, giving larger protein crystals," J. App. Cryst. 30:198-202 (1997).
Chayen, N. E. et al., "Comparative studies of Protein Crystallization by Vapour-Diffusion and Microbatch Techniques," Acta Cryst. D54:8-15 (1998).
Chayen, N. E. et al., Protocol: A novel technique for containerless protein crystallization, Protein Engineering 9(10):927-929 (1990).
Chayen, N. E. et al., "Recent advances in methodology for the crystallization of biological macromolecules," Journal of Crystal Growth, 1999, pp. 649-655, 1981199, Elsevier Science B.V., The Netherlands.
Chayen, N. E. et al., "Tackling the bottleneck of protein crystallization in the post-genomic era," Trends Biotech. 20(3):98 (2002).
Chayen, N. E., "The role of oil in macromolecular crystallization," Structure 5(10):1259-1274 (1997).
Cianci, M. et al., "Structure of lobster apocrustacyanin $A_1$ using softer X-rays," Acta Cryst. D57:1219-1229 (Apr. 2001).
Cox, M. J. et al., "Experiments with Automated Protein Crystallization," J. Appl. Cryst. 20:366-373 (1987).
Cox, M. J. et al., "An Investigation of Protein Crystallization Parameters using Successive Automated Grid Searches (SAGS)," J. Cryst. Growth 90(1-3):318-324 (1988).
Cudney, B. et al., "Screening and Optimization Strategies for Macromolecular Crystal Growth," Acta Cryst. D50:414-423 (1994).
D'Arcy, A., "Crystallizing Proteins a Rational Approach?," Acta Cryst. D50:469-471 (1994).
DeLucas et al., "New High-throughput Crystallization Technology," (Abstract E0014 from ACA2002 Meeting), printed from http://www.hwi.buffalo.edu/ACA on Apr. 10, 2002 (1 page).
Diller, D. J. et al., "An accurate numerical model for calculating the equillibration rate of a hanging-drop experiment," Acta Cryst. D55:656-663 (1999).
Dong, J. et al., "Bound-solvent structures for microgravity-, ground control-, gel- and microbatch-grown hen egg-white lysozyme crystals at 1.8 A resolution," Acta Cryst. D55:745-752 (Apr. 1999).
Doubile, S. et al., "Crystallization and preliminary X-ray analysis of the 9 kDa protein of the mouse signal recognition particle and the selenomethionyl-SRP9," FEBS Letters, 1996, pp. 219-221, vol. 384, Federation of European Biochemical Societies.
Evans, P.R. et al., "Crystallographic Structure of Allosterically Inhibited Phosphofructokinase at 7A Resolution," J. Mel. Biol., 191:71 3-720 (1986).
Fiehn, H. et al., "Microsystem Technology for Pipetting Systems: Parallel Sample Treatment in the Submicroliter Range (25)," smallTalk2000 Association for Laboratory Automation Final Conference Program, San Diego, CA, held Jul. 8-12, 2000 (Abstract) (1 page).
Fujitsu Patent Abstracts of Japan "Method for Growing and Recovering Crystal," Pub. No. 3050177, Apr. 03, 1991, App. No. 01184155, Jul. 15, 1989.
Gaasterland, I., "Feasibility of Structure Genomics and Impact on Computational Biology: Post-Workshop Review," Mathematics and Computer Science Division, Argonne National Laboratory, Jan. 26, 1 998 printed from http://www-fp.mcs.anl.gov/~gaasterland/sg-review.html on Apr. 12, 2002 (7 pages).
Gaasterland, T., "Structural genomics: Bioinformatics in the driver's seat," Nat. Biotech. 16:625-627 (Jul. 1998).
German, A.L. et al., "A sampling valve for use in gas chromatography adaptable for high pressure or high — temperature," Journal of Physics E, Scientific Instruments, 1972, vol. 5, p. 413, The Institute of Physics, United Kingdom.
Gilliland, G. L. et al., "Screening For Crystallization Conditions and Robotics: Biological Macromolecule Crystallization Database, Version 3.0: New Features, Data and the NASA Archive for Protein Crystal Growth Data," Acta Cryst. D50:408-413 (1994).
Gonzalez, F. et al., "Crocodile: An Automated Apparatus for Organic Crystal Growth from Solution," Acta Astronautica 25(12):775-784 (1991).
Heinemann et al., Scientific concepts: The Berlin "Protein Structure Factory Initiative," printed from http://www.rzpd.de/psf/sconcept2.html on Dec. 21, 2001 (1 6 pages).
Jaklevic, J. et al., "Protein Microcrystallization and Structure Determination," Project No. 98045.
Jancarik, J. et al., "Sparse matrix sampling: a screening method for crystallization of proteins," J. Appl. Cryst. 24:409-411 (1991).
Jing, H. et al., "New structural motifs on the chymotrypsin fold and their potential roles in complement factor B," EMBO J. 19(2):164-173 (2000).
Jing. H. et al., "Structural basis of profactor D activation: from a highly flexible zymogen to a novel self-inhibited serine protease, complement factor D," Euro. Mol. Sic. Org. 18(4):804-814 (1999).
Jing, H. et al., "Structures of Native and Complexed Complement Factor D: Implications of the Atypical His57 Conformation and Self-Inhibitory Loop in the Regulation of Specific Serine Protease Activity," J. Mol. Biol. 282: 1061-1081 (1998).
Jones et al., "Fully Automated Preparation of Hanging Drop Protein Crystallization Plates," abstract from ACA01 meeting printed from http://www.hwi.buffalo.edu/ACA/ACA01/abstracts/text/W0352.html on Aug. 26, 2002 (1 page).
Jones, N., et al., "Apocalypse now: update on automated protein Crystallization using the new ACA vapor diffusion plate," Acta CrystallogrA (1987) 43 (Supplement):0275.
Kam et al., "On the Crystallization of Proteins," J. Mol. Biol. 123:539-555 (1978).
Kelders, HA. et al., "Automated protein crystallization and a new crystal form of a subtilisin; eglin complex," Protein Engin. 1 (4):301-303 (1987).
Kingston, R.L. et al., "Search Designs for Protein Crystallization Based on Orthogonal Arrays," Acta E C st., 1994, 429-440, Section D50, International Union of Crystallography, Great Britain.
Koltay, P., "A Novel Fixed Volume Dispenser for the Massive Parallel Liquid Handling of Nanoliter Volumes," (Abstract for presentation scheduled for Oct. 25, 2001) printed from http://www.eurotabautomation.org on Apr. 11, 2002 (2 pages).
Korkhin, Y.M. et al., "Microseeding Crystallization of a protein by microseeding after establishing its phase diagram," in Research Report 1 (Aug. 95), printed from http://www.douglas.co.ukl.repl.html on Apr. 11, 2002 (6 pages).
Kwong, P.D. et al., "Probability Analysis of Variational Crystallization and its Application to gpl2O, the Exterior Envelope Glycoprotein of Type 1 Human immunodeficiency Virus (HIV-1)," Journal of Biological—Chemistry, Feb. 12, 1999, pp. 4115-4123, vol. 274, No. 7, American Society for Biochemistry and Molecular Biology, Inc., U.S.
Leonidas, D.D. et al., "Refined Crystal Structures of Native Human Angiogenin and Two Active Site Variants: Implications for the Unique Functional Properties of an Enzyme Involved in Neovascularisation During Tumour Growth," J. Mol. Biol. 285:1209-1233 (1999).
Lloyd, L. F. et al., "Many Crystal Forms of Human Immunodeficiency Virus Reverse Transcriptase," J. Mol. Biol. 217(1):19-22(1991).
Lowe, J. et al., "Capital Equipment MRC Laboratory of Molecular Biology Nov. 4, 2001" (4 pages).

Luft "Microbatch macromolecular crystallization on a thermal gradient," *Journal of Crystal Growth* Jan. 15, 1999, vol. 196, No. 2-4, North Holland Pub. Co., Amsterdam, NL.

Luft et al., "High Throughput Protein Crystallization: Keeping up with the Genomics," (Abstract for presentation to be given at Gordon Research Conference "Diffraction Methods in Molecular Biology" on Jul. 3, 2000 at Andover, NH, USA)) printed from http://www.imca.aps.anl.gov/-ahoward/luft_ab.html (1 page).

Luft et al., "Macromolecular crystallization in a high throughput laboratory—the search phase," *J. Cryst. Growth* 232:591-595 (2001).

Luft et al., "Microbatch macromolecular crystallization in micropipettes," *J. Cryst. Growth* 196:450-455 (1999).

Luft et al., "Microbatch macromolecular crystallization on a thermal gradient," *J. Cryst. Growth* 196:447-449 (1999).

Luo, M., "Structural Genomics of *C. elegans*," (Abstract W0027 from ACA2002 Meeting) printed from http://www.hwi.buffalo.edu/ACNACA02/abstracts/text/W0027.html on Apr. 10, 2002 (1 page).

McPherson, A., "Crystallization of Macromolecules: General Principles," in *Methods in Enzymology* 114:112-120(1985).

McPherson, A., "Crystallization of Proteins by Variation of pH or Temperature," in *Methods in Enzymology* 114:125-1 27 (1985).

McPherson, A., "Two approaches to the rapid screening of crystallization conditions," *J. Cryst. Growth* 122:161-1 67 (1992).

McPherson, A., "Use of Polyethylene Glycol in the Crystallization of Macromolecules," in *Methods in Enzymology* 114:120-125 (1985).

Meeting Summary: "NIGMS Structural Genomics Project Planning Meeting.The Protein Structure Initiative, Bethesda, MD, Nov. 24, 1998," printed from http://www-nmr.cabm.rutgers.edu/labdocuments/mtgsummaries/nigms/nigms.html on Apr. 12, 2002 (17 pages).

Meeting Summary: "NIH Protein Structure Initiative Meeting: Target Selection, Feb. 1 999, Washington, D.C." printed from http://www-nmr.cabm.rutgers.edu/labdocuments/mtgsummaries/nih,prot_struct_nit/nih on Apr. 12, 2002 (23 pages).

Montelione, G.T. et al., "Structural genomics: keystone for a Human Proteome Project," *Nat. Struct. Biol.,* 6(1):11-12 (Jan. 1999).

Morris, D.W. et al., "Automation of Protein Crystallization Trials: Use of a Robot to Deliver Reagents to a Novel Multi-Chamber Vapor Diffusion Plate," *Biotechniques* 7(5):522-527 (1989).

Mueller et al., "Development of a technology for automation and miniaturization of protein crystallization," *J. Biotech.* 85(1):7-14 (2001).

Newman, AR., "Send in the Robots," *Anal. Chem.* 62(1):29A-34A (1990).

News Release: "Large-scale Xn: The use of Microbatch for Large Scale Crystallization Projects," Douglas Instruments, Hungerford, UK (indicated on website as news from Feb., 99), printed from http://www.douglas.co.uklproposal.html on Feb. 22, 2001 (5 pages).

Nyarsik et al., "High Throughput Screening Station for Automated Protein Crystallization," (Abstract) (1 page).

Oct. 2, 2002 Press Release: "Minutes Apr. 22-23, 1999 Biological and Environmental Research Advisory Committee (BERAC)," this meeting was announced in the Federal Register for Apr. 22-23, 1999 (Public Law 92-463, 86 Stat. 770) American Geophysical Union, Washington, D.C., printed from http://www.er.doe.gov/production/ober/berac/4-99mins.html on Apr. 12, 2002 (8 pages).

Oldfield, T.J. et al., "A Flexible Approach to Automated Protein Crystallization," *J. Appl. Cryst.* 24:255-260 (1991).

Pebay-Peyrouta, E. et al., "X-ray Structure of Bacteriorhodopsin at 2.5 Angstroms from Microcrystals Grown in Lipidic Cubic Phases," *Science* 277:1676-1681 (1997).

Perrakis, A. et al., "Protein microcrystals and the design of a micro-diffractometer: current experience and plans at EMBL and ESRF/IDI3," *Acta Cryst.* D55:1765-1770 (1999).

Presentation by Chair Graham Fleming, University of California, Berkeley: "Working Group on Biosciences," pp. 175-198, printed from http://www-als.lbl.gov/als/workshops/scidirecthtml/9BioSci/Word_Work _File_L_646, index of /als/workshops/scidirecthtml/9BioSci indicates file available in multiple formats, indicates file last modified Nov. 1998.

Presentation: NASA, Marshall Space Flight Center Lab-on-a-Chip Based Protein Crystallization, by van der Woerd, M., dated Oct. 25, 2001, printed from worldwideweb in 2002 (27 pages).

Press Release: "Berkeley Lab Research Review Summer 2000 The Crystal Robot," by Preuss, P., printed from http://www.lbl.gov/Science-Articles/Research-Review/Magazine/2000/Winter/features on Feb. 28, 2002 (3 pages).

Press Release: "Bringing the Genome to Life Report From the Archives Bringing the Genome to Life Energy Related Biology in the New Genomic World, A New Research Program for the Department of Energy's Office of Biological and Environmental Research recommended by the Biological and Environmental Research Advisory Committee (Jun. 2000)" printed from http://doegenomestolife.org/history/genome-to-life-rpt.html on Apr. 12, 2002 (23 pages).

Press Release: "Crystallomics Core@ JCSG Crystallomics Core," printed from http://bioinfo-core.jcsg.org/bic/links/crystallomics.htm on Feb. 25, 2002 (2 pages with page indicating links last updated Apr. 18, 2001).

Press Release: "For Immediate Release (Sep. 25, 2000): Joint Center for Structural Genomics Funded to Advance High-Throughput Protein Structure Determination," printed from http://www.sdsc.edu/Press/00/092600.html on Feb. 26, 2002 (3 pages).

Press Release: "Large-scale Xn The use of Microbatch for Large-Scale Crystallization Projects," by Douglas Instruments printed from http://douglas.co.uk/proposal.htm on Apr. 11, 2002 (5 pages).

Press Release: "PBD/Research/Research Areas/AUTOMATION," printed from http://www.lbl.gov/LBL—Programs/pbd/xl_research/automation.html on Feb. 28, 2002 (4 pages).

Press Release: Products Feb. 2001 printed from http://www.douglas.co.ukproducts.html on Mar. 2, 2002 (2 pages).

Press Release: "RAMC 1999 Presentation Abstracts Presentation Ti—Ti6" printed from http://www.hamptonresearch.com/stuff/RAMC99/RAMC99TA.html on Apr. 8, 2002 (11 pages).

Press Release: "RAMC 2001 Poster Abstracts," printed from http://www.hamptonresearch.com/stuff/RAMC01/RAMC01PA.html on Apr. 10, 2002 (17 pages).

Press Release: "RAMC 2001—Presentation Abstracts Presentations T1—T15" printed from http://www.hamptonresearch.com/stuff/RAMO01/RAMO01TA.html on Apr. 8, 2002 (12 pages).

Press Release: "Research and Innovation: Genomics Institute of the Novartis Research Foundation (GNF), Novartis Institute for Genomics," (copyright, 1999) printed from http://www.pharma.novartis.com/research on Dec. 18, 2001 (2 pages).

Press Release: "Response to a Dec. 8, 2000, charge from the Director of the DOE Office of Science," printed from http://www.er.doe.gov/production (19 pages).

Press Release: "Structural Biology—Charge Jun. 10, 1997—Report of the Structural Biology Subcommittee of the Biological and Environmental Research Advisory Committee—In response to the charge letter of Dr. Martha Krebs, Jun. 10, 1997," printed from http://www.er.doe.gov/production/ober/berac/final697.html on Feb. 26, 2002 (29 pages).

Press Release: "System Users MPAX and Oryx Users Feb. 2002," printed from http://www.douglas.co.uklusers.htm on Mar. 2, 2002 (3 pages).

Press Release: "TECAN Compound dissolution Automating Drug Discovery at Zeneca," (Oct. 1998) printed from http://www.tecan.com/pr/tecprDDElisa.html on Apr. 15, 2002 (1 page).

Press Release: "TECAN GENESIS Workstation Genesis Workstation," printed from http://www.tecan.com/tecmain.genesis_workstation.html on Apr. 15, 2002 (1 page).

Press Release: "The Robot X-ray Crystallography in Leiden," printed fro http://www.chem.com.Leidemuniv.nl/bfsc/robot.html on Mar. 2, 2002 (2 pages).

Press Release: "The Scripps Research Institute News and Views Life After the Human Genome Project: TSRI Researchers Spearhead Protein Structure Initiative," by Mika One Benedyk, printed from http://www.scripps.edu/newsandviews/e_20010226/printjcsg.html on Feb. 28, 2002 (3 pages).

Press Release: "Winners NASA Selects Research Proposals in Cellular and Macromolecular Biotechnology" printed from _http://research.hq.nasa.gov/code_u/nra/current/NRA-00-HEDS-03/winners.html on Apr. 8, 2002 (5 pages).

Press Release: East of England Innovation Relay Centre: Pharma Technology Otters from Europe, particularly High-throughput protein crystallization screening and polymorph screening (Reference: PAN4159) on p. 15 of document printed from http://www.stjohns.co.uk/eeirc/pharma%20offers.htm on Apr. 11, 2002 (32 pages).

Press Release: Functional Genomics http://www.bmb.psu.edu/simpson/i6genome/Function.html (1 page).

Press Release: High-throughput protein crystallization screening and ploymorph screening http://www.steinbeis-europa.de/db/ircnet_details.php?BEREICH=LIFE&TYP=Offer&BB (Abstract).

Press Release: Lab Automation 2001—Annual Conference and Exhibition Lab Automation 2002 Jan. 26-30, 2002 Palm Springs California "Preliminary Poster Program" printed on Apr. 11, 2002 from http:www.labautomation.org/LA/LAO2/program/action.lasso?-database LA2002Abs&-layout Apr. 11, 2002d (166 pages).

Press Release: Letter to DOE Health and Environmental Research Advisory Committee Chairman dated May 28, 1998, printed from http://www.er.doe.gov/production/ober/berac/stbiochg.html on Feb. 26, 2002 (2 pages).

Press Release: Letter to DOE Health and Environmental Research Advisory Committee Chairman dated Jun. 10, 1997, printed from http://www.er.doe.gov/production/ober/berac/stbiochg.html on Feb. 26, 2002 (2 pages).

Press Release: Minutes Nov. 5-6, 1998 Biological and Environmental Research Advisory Committee (BERAC). The meeting was announced in the Federal Register for Nov. 5-6, 1998 (Pub. L. No. 92-463, 86 Stat. 770) American Geophysical Union, Washington, D.C., printed from http://www.er.doe.gov/production/ober/berac/i1-5-98mins.html on Apr. 12, 2002 (15 pages).

Press Release: Stewart, P.S. et al., "Using Microbatch for Large-Scale Crystallization Projects," Large-scale xn.visual printed from http://www.douglas/co.uk/glasgow.htm Aug. 1, 2002 (3 pages).

Press Release: Structural Biology, Charge May 28, 1998 Report of the Structural Biology Subcommittee of the Biological and Environmental Research Advisory Committee In response to the charge letter of Dr. Martha Krebs, May 28, 1998 Executive Summary Improvements recommended for current beam lines http://www.er.doe.gov/production/ober/berac/final598.htm (11 pages).

Press Release: Tecan Genesis NPS Nanopipetting for plate and array-based applications: *Miniaturize your Application 1 with GENESIS NPS* printed from http://www.tecan.com/tecmainnps.html on Apr. 13, 2002 (3 pages).

Press Release: Tecan Product News Product News from 1998 printed from http://www.tecan.com/tec.mainproduct_news_98.html Apr. 13, 2002 (3 pages).

Press Release: Tecan Product News Product News from 1999 printed from http://www.tecan.com/tec_mainproduct_news_99.html Apr. 13, 2002 (3 pages).

Press Release: Tecan Product News Product News from 2000, printed from http://www.tecan.com/tec_mainproduct_news_00.html Apr. 13, 2002 (2 pages).

Pusey, M. et al., "Growth Kinetics of Tetragonal Lysozyme Crystals," *J. Cryst. Growth* 76:593-599 (1986).

Pusey, ML. et al., "Protein Crystal Growth Growth Kinetics for Tetragonal Lysozyme Crystals," *J. Biol. Chem.* 261 :6524-6529 (1985).

Rawas, A. et al., "Preliminary Crystallographic Studies on Duck Ovotransferrin" *J. Mol. Biol.* 208:213-214 (1989).

Report entitled, "Physical Biosciences Division," particularly section entitled " Protein Microcrystallization Robotic System," (pp. 14-17), printed from http://www-nsd.lbl.gov/LBL-Publications/LDRD/1 998/PB/index.html#Jaklevic, on Aug. 28, 2002, page indicated as last modified on Feb. 19, 1999 (17 pages).

Rippon, G.D. et al., "Improved Microdroplet Method for Quantitative X-Ray Microanalysis of Small Fluid Samples," *Micron* 24(1):17-21 (1993).

Rosenbaum, D.F. et al., "Protein interactions and crystallization," Journal of Crystal Growth, 1996, pp. 752-758, vol. 169, Elsevier Science B.V., The Netherlands.

Rost, B., "Marrying structure and genomics," *Structure* 6:259-263 (1998).

Rubin, B. et al., "Minimal Intervention robotic protein crystallization," *J. Cryst. Growth*. 110:156-163 (1991).

Sali, A., "100,000 protein structures for the biologist," Avalon Meeting Review, document generated Jan. 22, 1998, printed Apr. 1, 1999 from http://guitar.rockefeller.edu/avalon/review/avalon.html (7 pages).

Sanchez et al., "Protein structure modeling for structural genomics," *Nat. Struc. Bid.* (*Structural Genomics Supplement*) 986-990 (2000).

Sanjoh "Spatiotemporal Protein Crystal Growth Studies suing Microfluidic Silicon Devices" *Journal of Crystal Growth* Jan. 15, 1999 pp. 691-702 vol. 196, No. 2-4, North Holland Publ co. Amsterdam, NL.

Santarsiero, B. D. et al., "Protein Micro-Crystallization Robotics System," WO251 Protein Micro-Crystallization Robotics System (09.07: Crystallization Techniques-Lectures-Room 106- Thursday, May 27 (Abstract for AC99 meeting) printed from http://www.hwi.buffalo.edu/ACNACA99/abstracts/text/WO251.html on Feb. 28, 2002 (2 pages) (webpage indicates last updated on May 18, 1999).

Saridakis, B. et al., "Improving protein crystal quality by decoupling nucleation and growth in vapor diffusion," *Protein Sci.*, 9:755-757 (2000).

Schuetz et al., "A novel nano-pipeting system for the development of high quality BioChip *arrays*," printed from www.tecan.com/la2000_nanopip.pdf (1 page).

Section of Report entitled, "Protein Microcrystallization and Structure Determination," printed from http://www—nsd.lbl.gov/LBL—Publications/LDRD/1999/PBD.html#Stevens on Aug. 28, 2002, page indicated as last modified on Apr. 4, 2000 (3 pages).

Shapiro, L. et al., "The Argonne Structural Genomics Workshop: Lamaze class for the birth of a new science," *Structure* 6(3):265-267 (1998).

Shieh, H.-S. et al., "Using Sampling Techniques in Protein Crystallization," Acta Cryst., 1995, pp. 305-3 10, 7 Section D51, International Union of Crystallography, Great Britain.

Shumate, "Low-vol. (nanoliter) automated pipeting," *Am. Biotechnol Lab.* 11(6):14 (1993).

Sibille, L., et al., "Solvent evaporation rates in the closed capillary vapor diffusion method of protein crystal growth," *J. Cryst. Growth* 110:80-88 (1991).

Snell, E.H. et al., "Partial Improvement of Crystal Quality for Microgravity-Grown Apoccrustacyanin C~" *Acta Cryst.*, D53:231-239 (1997).

Soriano, T. et al., "ASTEC: an Automated System for Sitting-Drop Protein Crystallization," J. Appl. Cryst., 1993, p. 558-562, vol. 26, International Union of Crystallography, Great Britain.

Stevens et al., "Global Efforts in Structural Genomics," *Science* 294:89-92 (2001).

Steven, "High-throughput protein crystallization," (review), *Curr. Opin. Struct. Biol.* 10(5):558-563 (2000).

Stevens, R.C. et al., Research Proposal for development and testing of a system of robotics workstations dedicated to protein crystallization., E.O. Lawrence Berkeley National Laboratory and The Scripps Research Institute, pp. 2, 29-31, 33-52 (unknown date).

Stevenson, "The world of Separation Science- Lab Automation '01: A Market Preparing for transition?," pp. 4-5 (2001).

Stewart et al., "Practical experimental design techniques for automatic and manual protein crystallization," *J. Cryst. Growth* 196:665-673 (1999), printed from http://www.douglas.co.uklrat_des.html on Mar. 2, 2002 (12 pages).

Stura, E.A. et al., "Reverse Screening," *Acta. Cryst.* D50:448-455 (1994).

Swartzendruber, J.K., et al., "Apocalypse: an automated protein crystallization system. III. In the beginning: The genesis of software," 1988 p. 81, Abstract PF5, Annual Meeting of the American Crystallographic Association, Philadelphia, PA.

Tebbutt J.S. et al., "Monitoring of crystallisation phenomena by ultrasound," *Electron. Left.* 35(1):90-92 1999.

Tisone, TC., "Dispensing systems for miniaturized diagnostics," *IVD Technology Magazine,* printed from http://devicelink.com/ivt/archive/98 (IVDI archive, May 98).

Tisone, TO. et al., "The Role of Non Contact Microfluidics in High Throughput Protein Crystallization,"(Abstract WO282 from ACA2002 Meeting) printed from http://www.hwi.buffalo.edu/ACAIACAO2/abstracts/text/WO282.htmt on Apr. 10, 2002 (1 page).

van der Woerd, M. et al., "About Small Streams and Shiny Rock: Macromolecular Crystal Growth in Microfluidics," (Abstract WO21 0 from ACA2002 Meeting) printed from http://www.hwi.buffalo.edu/ACA/ACA02/abstracts/textW0210.html.

van der Woerd, M.J., "Lab—on—a—chip Based Protein Crystallization [P—66],"*smallTalk2001 Association for Laboratory Automation Final Conference Program,* San Diego, CA, held Aug. 27-31, 2001 (Abstract) (2 pages).

Varadarajan, R. et al., "Crystallographic Structures of Ribonuclease S Variants with Nonpolar Substitution at Position 13: Packing and Cavities," *Biochem.* 31(49): 12315-12326 (1 992).

Villasensor et al., "Fast Drops: A Speedy Approach to Setting Up Protein Crystallization Trials," (Abstract W0309) from ACA01 meeting printed from http://www.hwi.buffalo.edu/ACA/ACA01/abstracts/text/W0309.html on Dec. 21, 2001 (1 page).

Ward, KB. et al., "Automatic Preperation of Protein Crystals Using Laboratory Robotics and Automated Visual Inspection," *J. Cryst. Growth* 90:325-339 (1988).

Ward, KB. et al., "Automating crystallization experiments," In Crystallization of Nucleic Acids and Proteins: A Practical Approach eds. A. Ducruiz & R. Giege, Oxford Univ. Press, New York, pp. 291-310.

Weber, P.C., "Overview of Protein Crystallization Methods," *Methods in Enzymology* 276:13-22 (1997).

Weber, P.C., et al., "Experiments with automated protein crystal growth," (1987) p. 28, Abstract H5, Annual Meeting of the American Crystallographic Association, Philadelphia, PA.

Webpage: "Harvesting, Harvesting Crystals from Microbatch for Cryocrystallography," Douglas Instruments Research Report 3, Oct. 1995, printed from http://www.douglas.co.uklrep3.htm on Apr. 11, 2002 (4 pages).

Webpage: "Poster Session 7 Genomics, Proteomics and New Target Discovery," The Society for Biomolecular Screening 7th Annual Conference and Exhibition (2001), see #701 4-701 5, printed from http://www.hwi.buffalo.edu/ (5 pages).

Webpage: Eickhoff et al., "An Automated Platform for Miniaturized protein Crystallization," Greiner Bio-One (Abstract), date of last modification on web indicated as Mar. 30, 2001, printed May 2002 (1 page).

Website listing Abstracts for Oral Presentations: 87 Instrumentation Instrumentation and Techniques for Crystallization pp. 1-3 (Nancy 2000 XIX European Crystallographic Meeting (held Aug. 25-31).

Website listing products available from Gilson, printed from http://www.gilson.com/cyberprd.htm on Feb. 22, 2001 (1 page).

Website: "Impax: IMPAX 1-5 for Crystallization with Microbatch" printed from http://www.douglas.co.uklimpax.htm on Mar. 2, 2002.

Website: "A day on High-Throughput Techniques in Structural Biology," printed from http://www.embi-heidelberg.de/courses/StructureSolution02/satelite.html (5 pages) text dated Aug. 1998 and Feb. 1999.

Website: "A Recipe to grow crystals of lysozyme by the gel acupuncture technique: Granada Crystallization box," printed from http://www.lec.ugr.es/GranadaCrystBox/GCB on Apr. 11, 2002 (7 pages).

Website: "Differences The Major Differences between Oryx6 and IMPAX 1-5," Douglas Instruments, dated Mar. 2001, printed from http://www.douglas.co.ukldifferent.html on Apr. 11, 2002 (1 page).

Website: "General Interest Invited Abstracts," (Jul. 26, 2001) printed from http://www.hwibuffalo.edu/ACA'ACAOl/abstracts on Apr. 13, 2002 (2 pages).

Website: "Harima Workshop on Implementation for High-throughput Structure Determination by Protein Crystallography—Present Status and Future Goal—A Satelite of International Conference on Structural Genomics 2000 at Spring-8" printed from http://www.spring8.or.jp/english/conference on Dec. 19, 2001 (4 pages).

Website: "News" printed from http://www.douglas.co.uklnews.htm on Apr. 15, 2002 (2 pages).

Website: "Oryx 6- Using Oryx 6 for Crystallization with Microbatch: Microbatch operation in identical to IMPAX 1-5" printed from http://www.douglas.co.uk/oryx.htm.

Website: "PhysicsWeb Protein crystallography: the human genome in 3—D," http://www.physicsweb.org/article/world1 1/5/8 (May, 1 1998), printed from website Apr. 11, 2002 (9 pages).

Website: Publications Journals Trade Journals: Events Index-Abstracts and Proceedigns Achema 2000, printed from http://www.combichem.net/files/abstract.htm on Aug. 1, 2002 (18 pages).

Website: BioRobotics http://www.biorobotics.com (Pamphlet), printed on Oct. 7, 1999 (12 pages).

Website: Garcia-Ruiz, J.M., "The role of gravity in protein crystallization: Is there an effect of gravity on the crystallization process," printed from http://lec.ugr.es/esatt/RoleoLgravity/Role.htm on Apr. 11, 2002 (3 pages).

Website: Micro-Arraying with the *Micro* Grid http://www.biorobotics.com/MicroArray.html, printed Oct. 20, 1999 (6 pages).

Wilson, S.A. et al., "Crystallization of and Preliminary X-ray Data for the Negative Regulator (AmiC) of the Amidase Operon of *Pseudomonas aeruginosa,"J. Mel. Biol.* 222(4):869-871 (1991).

Yakovlev Y.O. et al., "A Laboratory Apparatus for Crystal Growth From Solution," Instruments and Experimental Techniques, 1998, p. 292-296, vol. 41, No. 2, Interperiodica Publishing, Russia.

Yeglan, D, "Task-specific robotics for sample loading, centering and retrieval," printed from http://www.smb.slac.stanford.edu/jcsg/robotics/abstracts/dyabs.html on Apr. 12, 2002 (1 page) (site last modified Oct. 16, 2000).

Zeelen, J. Ph. et al., "Crystallization Experiments with 2-Enoyl-CoA Hydralase, Using an Automated 'Fast-Screening' Crystallization Protocol," *Acta Cryst.* D50:443-447 (1994).

Zeppezauer, M., "Microdiffusion cells for the growth of single protein crystals by means of equalibrium dialysism" Arch. Biochem., Biophys. (1968) 564-573.

"RAMC 1999—Round Table Notes," particularly regarding Robotics (starting at bottom of $1^{st}$ page), printed from http://www.hamptonresearch.com/stuff/RAMC99TRN.html.com on Aug. 21, 2002 (7 pages).

Abbott, "Structures by numbers," Nature 408: 130-132 (Nov. 9, 2000).

Abola et al., "Automation of X-ray crystallograph," Nat. Struc. Biol. (Structural Genomics Supplement: 973-977 (Nov. 2000

Mochalkin et al., "High-Throughput Structure Determination in an Informatics Environment," (2001) print from http://www.accelrys.com webzine on Jun. 1, 2002 (4 pages).

Ahn et al., Fluid Micropumps Based on Rotary Magnetic Actuators, Proceedings of 1995 IEEE Micro Electro Mechanical Systems Workshop (MEMS '95), held in Amsterdam, Netherlands on Jan. 29-Feb. 2, 1995, pp. 408-412 (1995).

Andersson et al., "Consecutive Microcontact Printing—Ligands for Asymmetric Catalysis in Silicon Channel," Sensors and Actuators, B, 3997, 2001, pp. 1-7.

Bellec et al., "In situ time-resolved FTIR spectroelectrochemistry: study of the reduction of TCNQ," Electrochem. Commun. 3:483-488 (2001).

Benard et al., "A Titanium-Nickel Shape-Memory Alloy Actuated Micropump," Proceedings of Transducers '97, 1997 International Conference on Solid-State Sensors and Actuators, held in Chicago, Illinois, Jun. 16-19, 1997, 1:361-384 (1997).

Bordin et al., "Identification and quantification of major bovine milk proteins by liquid chromatography," J. Chromatograph A 928:63-76 (2001).

Boussad et al., "High-Resolution Multiwavelength Surface Plasmon Resonance Spectroscopy for Probing Conformational and Electronic Changes in Redox Proteins," Anal. Chem. 72:222-226 (2000).

Brandt, D.W., "Multiplexed nanoliter transfers for high throughput drug screening using the Biomek 2000 and the high density replicating tool," J. Biomol. Screen 2:111-116 (1997).

Brechtel et al., "Control of the Electroosmotic Flow by Metal-salt-containing Buffers," J Chromatography A, 716:-97-105 (1995).

Brochure: "Jasco—Pioneering in modern protein science: UV/Vis, FTIR, Raman, CD," Unverified date.

Bryzek et al., "Micromachines on the March," 8045 IEEE Spectrum, 31(5) 20-31 (1994 XP 0004546261.

Buchaillot et al., "Silicon Nitride ThinFilms Young's Modules Determination by an Optical Non-Destructive Method," Jpn. J. Appl. Phys., 36 Pt. 2(6B):L794-:L797 (1997).

Carter et al., "Protein Crystallization Using Incomplete Factorial Experiments," Journal of Biological Chemistry, 1979, pp. 12219-12223, vol. 254, No. 23.

Carter et al., "Statistical Design of Experiments for Protein Crystal Growth and the Use of a Precrystallization Assay," Journal of Crystal Growth 90, 1998, pp. 60-73.

Chappell et al., "Quantitative analysis of chromium(V) by EPR spectroscopy," Talanta 46:23-28 (1998).

Chayen, N.E. et al., "Fish muscle structure: fibre types in flatfish and mullet fin muscles using histochemistry and antimyosin antibody labeling," J. Muscle Res. Cell Motility 14:53-542 (Oct. 1993).

Chayen, "The Role of Oil in Macromolecular Crystallization," Structure, 1997, vol. 5, No. 10, pp. 1269-1274.

Chiu et al., "Patterned Deposition of Cells and Proteins Onto Surfaces by Using Three-Dimensional Microfluidic Systems," PNAS, 97(6):2406-2413 (2000).

Chou et al., "A Microfabricated Device for Sizing and Sorting DNA Molecules," PNAS, 96: 11-13 (1999).

Clarke and Kane, "Optical detection of membrane diopole potential: avoidance of fluidity and dye-induced effects," Biochemica Biophysica Acta 1323(2):223-239 (Jan. 31, 1997).

Codina et al., "Combined use of ESI-MS and UV diode-array detection for localization of disulfide bonds in proteins: application to an $\alpha$-L-fucosidase of pea," J. Peptide Res. 57:473-482 (2001).

D'Alessio et al., "Absorption spectroscopy of toluene pyrolysis," Optics and Lasers in Engineering 37:495-508 (2002).

Delamarche et al., "Patterned Delivery of Immunoglobulins to Surfaces Using Microfluidic Networks," Science, 276:779-781 (1997).

Ducruix et al., "Methods of Crystallization in Crystallization of Nucleic Acids and Proteins — A Practical Approach," IRL Press, Oxford. 1992.

Duffy et al., "Patterning Electroluminesence Materials with Feature Sizes as Small as 5 µm Using Elastomeric Membranes as Masks for Dry Lift —Off," Adv. Mater. 11(7):546-552 (1999). XP-000849014.

Duffy et al., "Rapid Prototying of Microfluidic Switches in Poly(dimethyl siloxane) and Their Actuation by Electro-Osmotic Flow," J. Micromech. Microeng., 9:211-217 (1999).

Duffy et al., "Rapid Prototyping of Microfluidic Systems in Poly(dimethylsiloxane), " Analytical Chemistry, 70(23):4974-4984 (1998).

Effenhauser et al., "Integrated Capillary Electrophoresis on Flexible Silicone Microdevices: Analysis of DNA Restriction Fragments and Detection of Single DNA Molecules and Microchips," Anal. Chem., 69(17):3451-3457 (1997).

Effenhauser et al., "Integrated Chip-Based Capillary Electrophoresis," Electrophoresis, 18:2203-2213 (1997).

Eichoff, et al., "Development of a technology for automation and miniaturization of protein crystallization," J. Biotech 85(1):7-14 (2001).

Fahrenburg et al., "A Microvalve System Fabricated by Thermoplastic Molding," J. Micromech. Microeng., 5:169-171 (1995).

Feher and Kam, "Diffraction Methods for Biological Macromolecules," eds. Wyckoff and Hirs, Methods in Enzymology, eds. in chief Colonick and Kapler, 19785, Academic Press, Orlando, 77-113.

Fu et al., "A Microfabricated Fluorescence-Activated Cell Sorter," Nature Biotechnology, 17:1109-111 (1999).

Gass et al., "Integrated Flow-Regulated Silicon Micropump," Sensors and Actuators A, 4335-4338 (1994).

Gerlach, T., "Pumping Gases by a Silicon Micro Pump with Dynamic Passive Valves," Proceedings of Transducers '97, 1997 International Confernce on Solid-State Sensors and Actuators held in Chicago, Illinois, Jun. 16-19, 1997, 1:357-360 (1997).

Goll et al., "Microvalves with Blistable Buckled Polymer Diaphragms," J. Micromech. Microeng. 6:77-79 (1998).

Graveson et al., "Microfluids — A Review," J. Micromech. Microeng., 3:168-182 (1993).

Grube et al., "IR-spectroscopic studies of Zymomonas mobills and teval precipitate," Vibrat. Spectro. 28:277-254 (2000).

Harrison et al., "Micromachining a Miniaturized Capillary Electrophoresis-Based Chemical Analysis System on a Chip," Science, 261:895-897, (1993).

Hautala et al., "Measurement of aquatic humus content by spectroscopic analyses," Wat. Res. 34(1):246-254 (2000).

Hayakawa et al., "Protein determination by high-performance gel-permeation chromatography: applications to human pancreatic juice, human bile and tissue homogenate," J. Chromatography B 754:65-76 (2001).

Hayakawa et al., "Serum protein determination by high-performance gelpermeation chromatography," J. Chromatography B696:619-23 (1997).

Heremans and Heremans, "Pressure Effescts on the Raman Spectrum of Proteins: Stability of the Salt Bridge in Trysin and Elastase," J. Mol. Struct. 214:305-314 (1989).

Holler et al., "Synthesis and spectroscopic characterization of 2-(2'-hydroxyphenyl)benzazole isothiocyanates as new fluorescent probes for proteins," J. Photochem. Photobiol. A: Chem. 149:217-225 (2002).

Hornbeck et al., "Bistable Deformable Mirror Device," Spatial Light Modulators and Applications 1988 Technical Digest Series., vol. 8, Postconference Edition, Summaries of papers presented at the Spatial Light Modulators and Applications Topical Meeting, Jun. 15-17, 1988, Optical Society of America, pp. 107-110.

Hosokawa et al., "Handling of Picoliter Liquid Samples In a Poly(dimethylsiloxane)-Based Microfluidic Device," Anal. Chem. 71(20):4781-4785 (1999).

Ikuta et al., "Three Dimensional Micro Integrated Fluid Systems (MIFS) Fabricated By Stereo Lithography," IEEE Kyushu Institute of Technology, pp. 1-6 (1994).

Jacobson et al., "High-Speed Separations on a Microchip," Anal. Chem., 6(7):1114-1118 (1994).

Jacobson et al., "Microfluidic Devices for Electrokinetically Driven Parallel and Serial Mixing," Anal. Chem., 71(20):4455-4459 (1999).

Jancura et al., "Surface-enhanced resonanace Raman spectroscopy of hypocrellin A: an effect of excitation wavelength and pH," Spectrochimica Acta part A 54:1519-1526 (1998).

Jaramillo et al., "Crystallization and Cryocrystallography Inside X-ray capillaries," J. Appl. Cryst. (2001) 34, pp. 365-370.

Jerman H., "Electrically-Activated Normally-Closed Diaphragm Valves," Proceedings of Transducers, '91, 1991 International Conference on Solid-State Sensors and Actuators, pp. 1045-1046 (1991).

Jung et al., "Chemical and Physical Interactions at Metal/Self-Assembled Organic Monolayer Interfaces," Critical Reviews in Solid State and Material Sciences, 19(1):2-10 (1994).

Kamholz et al., "Quantitative Analysis of Molecular Interaction In a Microfluidic Channel: The T-Sensor," Analytical Chemistry, vol. 71, No. 23, Dec. 1, 1999, pp. 5340-5347.

Kenis et al., "Microfabrication Inside Capillaries Using Multiphase Laminar Flow Patterning," Science, 2985: 83-85 (1999).

Koltay, P., "A Novel Fixed vol. Dispenser for the Massive Parallel Liquid Handling of Nanoliter vols." (Abstract for presentation scheduled for Oct. 25, 2001) printed from http://www.eurolabautomation.org/ on Apr. 11, 2002 (2 pages).

Kopp et al., "Chemical Amplification: Continuous-Flow PCR on a Chip," Science, 260: 1046-1048 (1998).

Kudryavtsev et al., "Polarized Raman Spectroscopic Studies of Tetragonal Lysozyme Single Crystals," Acta Cryst. D54:1216-1229 (1999).

Kudryavtsev, et al., "The effect of ordering of internal water in thaumalin and lysozyme crystals as revealed by Raman method," J. Crystal Growth 219(1-2):102-114 (Oct. 1, 2000).

Kuhn et al., "Silicon Charge Electrode Array for Ink Jet Printing," IEEE Transactions on Electron Devices, ED-25(10):1257-1260 (1978).

Lin et al., Convective-diffusive transport in protein crystal growth, Journal of Crystal Growth, 151 (1995), pp. 153-162.

Lin et al., "Free-Space Micromachined Optical Switches for Optical Networking," IEEE J. Selected Topics in Quantum Electronics, 5(1):4-9 (1999).

Lis, "Luminescence spectroscopy of lanthanide(III) ions in solution," J. Alloys Comp. 341: 45-50 (2002).

Lotters et al., "The Mechanical Properties of the Rubber Elastic Polymer Polydimethylsiloxane for Sensor Applications," J. Micromech. Microeng. 7:145-147 (1997).

Lucy et al., "Characterization of the Cationic Surfactant Induced Reversal of Electroosmotic Flow in Capillary Electrophoresis," Anal. Chem. 68: 300-305 (1996).

Luft et al., "Kinetic Aspects of Macromolecular Crystallization," Methods in Enzymology, 1997, pp. 110-130, vol. 276.

Luft et al., "Microbatch Macromolecular Crystallization in Micropipettes," Journal of Crystal Growth, 196 (1999), pp. 450-455.

Mach et al., "Detection of Proteins and PHenol in DAN Samples with Second-Derivative Absorption Spectroscopy," Anal. Biochem. 200:20-26 (1992).

Maluf et al., "An Introduction to Microelectromechanical Systems Engineering," Artech House Publishers, Boston London pp. 42-45.

Markx et al., "Applications of Dielectrophoresis in Biotechnology," Tibtech., 15:426-432 (1997).

McPherson et al., "Crystallization of Proteins by Variations of pH of Temperature," Methods Enzymol., 1985, 114: pp. 120-125.

McPherson, "Crystallization of Macromolecules: General Principles," Methods Enzymol., 1985, pp. 114, 112.

Menezes, et al., "Identification and Entity Authentication," Handbook of Applied Crytograph, CRC Press Chapter 10 pp. 405-417 (1996) XP002258705.

Miller et al., "A Comparison between Protein Crystals Grown with Vapor Diffusion Methods in Microgravity and Protein Crystals using a Gel Liquid-liquid diffusion Ground-Based Method," Journal of Crystal Growth, 32 (1992), pp. 306-309.

Mino et al., "Hydrogen Bonding of Sulfur Ligands in Blue Copper and Iron-Sulfur Proteins: Detection by Resonance Raman Spectroscopy," Biochem, 26:8059-8065 (1987).

Miteva et al., "Spectrophotometric titration of Ionisable groups in proteins: a theoretical study," Spectrochimica Acta Part A 56:2033-2041 (2000).

Moffat and Ren, "Synchrotron radiation applications to macromolecular crystallography," Curr. Opin. Struct. Biol. 7:689-698 (1997).

Moffat et al., "Approaches towards the quantitative analysis of peptides and proteins by reversed-phase high-performance liquid chromatography in the absence of a pure reference sample," J. Chromatography A 891: 235-242 (2000).

Muller et al., "Surface-Micromachined Microoptical Elements and Systems," Proceedings of IEEE, 86(8): 1705-1720 (1998).

Needleman and Wunsch, "A General Method Applicable to the Search for Similarities in the Amino Acid Sequence of Two Proteins," J. Mol. Biol. 46:443-453 (1970).

Nerad et al., "Ground-Based Experiments on the Minimization of Convention During the Growth of Crystals From Solution," Journal of Crystal Growth, 1986, pp. 591-608, vol. 75.

Olsson et al., "Simulation Studies of Diffuser and Nozzle Elements for Valve-less Micropumps," Proceedings of Transducers '97, 1997 International Conference on Solid-State Sensors and Actuators, held in Chicago, Illinois, Aug. 16-19, 1997, 2:1039-1042 (1997).

Pandher et al., "Spectroscopy, persistent hole burning, and holographic applications of naphtophthalocyanine/haloanthracene systems," J. Lumin. 98:207-212 (2002).

Pearson and Lipman, "Improved tools for biological sequence comparison," Proc. Natl. Acad. Sci. USA 85:2444-2448 (Apr. 1988).

Phillips, "Crystallization in Capillary Tubes," Methods Enzymol. 1985: 114: pp. 128-131.

Platoff, Jr. et al., "Serial Capillary Gas Chromatography/Fourier Transform Infared Spectrometry/Mass Spectrometry (GC/IR/MS): Qualitative and Quantitative Analysis of Amphetamine, Methamphetamine, and Related Analogues in Human Urine," J. Anal. Toxicol. 16:389-397 (Nov./Dec. 1992).

Press Release: Jaklevic et al., "Protein Microcrystallization and Structure Determination," printed from http://www.berkeleylab.com/.

Press Release: "Structural Biology — Charge Jun. 10, 1997 —Report of the Structural Biology Subcommittee of the Biological and Environmental Research Advisory Committee — In response to the charge letter of Dr. Martha Krebs, Jun. 10, 1997," printed from http://www.er.doe.gov/production/ober/berac/final697.htm on Feb. 26, 2002 (29 pages).

Qin et al., "Photolithography with Transparent Reflective Photomasks," J. Vac. Sci. Technology, 16(1):98-103 (1996).

Qin et al., "Elastometric Light Valves* *," Adv. Matter., 9(5):407-410 (1997) XP-000683691.

Quake et al., "From Micro- to Nanofabrication with Soft Materials," Science, vol. 2990, pp. 1536-1540 (2000).

Rapp R., "LIGA micropump for gases and liquids," Sensors and Actuators A, 40:57-61 (1994).

Roylance et al., "A Batch-Fabricated Silicon Accelerometer," IEEE Transactions on Electron Devices, ED-26(12):1911-1917 (1979).

Rückert et al., "Characterization of protein mixtures by Ion-exchange chromatography coupled on-line to nuclear magnetic resonance spectroscopy," J. Chromatography A 840:131-135 (1999).

Ruiz et al., "Agarose as Crystallization Media for Proteins 1: Transport Processes," Journal of Crystal Growth, 2001, pp. 165-172, vol. 232.

Ruiz et al., "Investigations on Protein Crystal Growth by the Gel Acupuncture Method," Acta Crystallographica, 1994, pp. 484-490, Section D.

Salemme, "A Free Interface Diffusion Technique for the Crystallization of Proteins for X-Ray Crystallography," Archives of Biochemistry and Biophysics, 1972, pp. 533-539, vol. 151.

Sane et al., "A Holistic Approach to Protein Secondary Structure Characterization Using Amide I Band Raman Spectroscopy," Anal. Biochem. 269:255-272 (1999).

Sanjoh et al., "Spatiotemporal Protein Crystal Growth Studies using Microfluidic Silicon Devices," Journal of Crystal Growth, 196 (1999), pp. 691-702.

Sasic and Ozaki, "Short-Wave Near-Infrared Spectroscopy of Biological Fluids, 1. Quantitative Analysis of Fat, Protein, and Lactose in Raw Milk by Partial Least-Squares Regression and Band Assignment," Anal. Chem. 73:64-71 (2001).

Schasfoort et al., "Field-Effect Flow Control for Microfabricated Fluidic Networks," Science, 266:942-945 (1999).

Schueller et al., "Fabrication of Glassy Carbon Microstructures by Soft Lithography," Sensors and Actuators, 72(2):125-139 (1999).

Shoji et al., "Smallest Dead vol. Microvalves for Integrated Chemical Analyzing Systems," Proceedings of Transducers '91, 1991 International Conference on Solid-State Sensors and Actuators, pp. 1052-1055 (1991).

Shoji, S., "Fluids for Sensor Systems," Topics in Current Chemistry, 194:162-168 Springer Verlag Berlin Heidelberg (1998).

Smith and Waterman, "Comparison of Biosequences," Adv. Appl. Math 2:462-489 (1961).

Smits, J.G., "Piezoelectric Micropump with Three Valves Working Peristaltically," Sensors and Actuators, A21-A23:203-206 (1990).

Sohn et al., "Capacitance Cytometry: Measuring Biological Cells One By One," PNAS, 97(20):10687-10690 (2000).

Stevens, Raymond C., "Design of high-throughput methods of protein production for structural biology," Structure (with Folding & Design) 8(9):R177-R185 (Sep. 15, 2000) (Available online Sep. 8, 2000).

Thomas et al., "Distribution coefficients of Protein Impurities in Ferritin and Lysozyme Crystals Self-Purification in Microgravity," Journal of Crystal Growth 211 (2000), pp. 149-156.

Thomas, Jr., "Raman Spectroscopy of Protein and Nucleic Acid Assemblies," Ann. Rev. Biophys. Biomol. Struct. 28:1-27 (1999).

Thompson et al., "Remote microwave wavelength spectrometry using an infrared fibre optic telecommunication network," Anal. Chimica Acta 463:1-4 (2002).

Tufte et al., "Silicon Diffused-Element Piezoresistive Diaphragms," J. Appl. Phys., 33(11):3323-3327 (1962).

Tutorial On: the Role of Computation Biology in High-Throughput Structure Determination: Computation Before, During, and After Structural Genomics, The Role of Computational Biology in Structural Genomics, document dated Feb. 17, 1998, printed Apr. 1, 1999 from http://www.fp.mes.anl.gov/gasterland/sg-review-slides.htm (14 pages).

Unger et al., "Monolithic Microfabricated Valves and Pumps by Multilayer Soft Lithography," Science, vol. 288, pp. 113-116 (2000).

Van der Pol et al., "A Thermo-Pneumatic Actuation Principle for a Microminiature Pump and Other Micromechanical Devices,"Sensors and Actuators, 17:139-143 (1989).

Van der Pol et al., "Micro Liquid Handling Devices — A Review," Micro Systems Technologies, 90:799-805 (1990).

Van Iersel et al., "Determination of Absorption Coefficients of Purified Proteins by Conventional Ultraviolet Spectrophotometry and Chromatography Combined with ultrawavelength Detection," Anal. Biochem. 151:196-204 (1985).

Vieder et al., "A Pneumatically Actuated Micro Valve with a Silicone Rubber Membrane for Integration with Fluid-Handling Systems," Proceedings of Transducers '95, the 8th International conference on Solid-State Sensors and Actuators and Eurosensors IX, held in Stockholm, Sweden on Jun. 25-29, 1995., 2:284-286 (1995).

Wagner et al., "Protein mapping by two-dimensional high performance liquid chromatography," J. Chromatography A 893:293-305 (2000).

Ward et al., "Automatic Preparation of Protein Crystals Using Laboratory Robotics and Automated Visual Inspection," Journal of Crystal Growth 90 (1988), pp. 325-339.

Washizu et al., "Molecular Dielectrophoresis of Biopolymers," IEEE Transactions on on Industry Applications, 30(4):835-843 (1994).

Website: "High-Resolution UV Spectroscopy," http://www.physics.nist.gov/Divisions/DivB44/facilities/uvs/uvs.html unverified print date of Jul. 1, 2002.

Website: "Nobel Prize —User Prize" printed form http://www.douglas.co.uk/walker.htm on Mar. 2, 2002 (1 page).

Website: "Olympus Microscopes BX40 and BX50," http://www.incbjnc.com/pages/BX4050.html (Sep. 30, 2000).

Website: Garcia-Ruiz J.M., "The role of gravity in protein crystallization: is there an effect of gravity on the crystallization process," printed from http://lec.ugr.es/esat/Role_of_gravity/Role.html on Apr. 11, 2002 (3 pages).

Wrobel and Boguta, "Study of the influence of substituents on spectroscopic and photoelectric properties of zinc phthalocyanines," J. Photochem. Photobiol. A: Chem 6045:1-10 (2002).

Wu et al., "MEMS Flow Sensors for Nano-Fluidic Applications," Sensors and Actuators A 89, 2001 pp. 152-158.

Xia et al., "Micromolding in Capiliaries: Applications in Material Science," _J. American Chemical Society, 116:5722-5731 (1996).

Xia et al., "Micromolding of Polymers in Capalaries: Applications in Microfabrication," Chemistry of Materials, 8(7):1558-1587 (1998).

Xia et al., "Soft Lithography," Angew. Chem. Int. Ed., 37:551-575 (1998).

XP-002149048, Ultman's Encyclopedia of Industrial Chemistry, Sixth Edition, 1999 Electronic Release, 6 pages.

Yang et al., "A MEMS Thermopneumatic Silicone Membrane Valve," Proceedings of the IEEE 10th Annual Workshop of Micro Electro Mechanical Systems Workshop (MEMS '97), held Jan. 26-30, 1997 in Nagoya, Japan, pp. 114-118 (1997).

Yang et al., "A Mems Thermopneumatic Silicone Membrane Valve, Proceedings of IEEE 10th Annual International Workshop on MicroElectro Mechanical Systems, " Sensors and Actuators, A64(1):101-108 (1998).

Yazdi et al., "Micromachined Inertial Sensors," Proceedings of IEEE, 66(6):1640-1659 (1998).

Young et al., "Contoured Elastic-Membrane Microvalves for Microfluidic Networks Integration," J. Biomechanical Engineering, 121:2-6 (1999).

Zengerle et al., "A Micro Membrane Pump with Electrostatic Actuation," 1992 IEEE Conf. on Micro Electro Mechanical Systems, held Feb. 4-7, 1992 in Travemunde Germany, pp. 19-24.

Zengerle et al., "Performance Simulation of Microminiaturized Membrane Pumps," from 7th International Conference on Solid-State Sensors and Actuators held Aug. 7-10, 1993 in Yokohama, Japan, pp. 106-109.

* cited by examiner

METHOD FOR SCREENING CRYSTALLIZATION CONDITIONS IN SOLUTION CRYSTAL GROWTH

The present invention is a continuation-in-part of U.S. Ser. No. 09/543,326, filed Apr. 5, 2000 now abandoned, which claims priority to from U.S. Ser. No. 60/128,018, filed Apr. 6, 1999, both hereby expressly incorporated by reference.

FIELD OF THE INVENTION

The present invention relates to the crystallization of proteins in or from protein solutions. The present invention particularly relates to a method of screening a large number of protein crystal growth conditions which may be conducive to protein crystallization. Even more particularly, the present invention relates to a method which identifies one or more optimum protein crystal growth conditions, while at the same time using substantially less protein solution.

BACKGROUND OF THE INVENTION

The crystallization of proteins for structure-function studies and structure based drug design has become an increasingly important part of biotechnology research. When crystal growth is attempted for a new protein, the appropriate chemical conditions (i.e. protein concentration in solution, precipitate type and concentration, pH, and growth temperature) are unknown and have typically been determined by trial and error experimentation.

Typically 1000 or more different sets of crystal growth conditions are screened to determine conditions conducive to crystallization. The screening involves repetitive procedures that are extremely laborious and tedious. With present laboratory protein crystal growth equipment, each crystallization chamber requires about one micro-liter of protein solution. The protein solutions typically have concentrations in the range of 10 to 25 micrograms per microliter to facilitate crystal growth. Therefore, to screen 1000 samples typically requires between 10 and 25 milligrams of protein. This is a considerable and costly amount, especially for proteins that are difficult to isolate or generally express. A large percentage (about 50%) of the proteins cannot easily be expressed in milligram quantities.

Thus, it would be desirable to provide methods for screening protein crystal growth conditions that require picogram to microgram amounts of protein for each screening condition. Preferably such methods would require only picogram to nanogram amounts of protein in picoliter to nanoliter volumes in each screening condition sample.

It would be further desirable to provide high throughput screening methods for screening protein crystal growth conditions in a large number of samples on a sub-microgram scale. These methods would use a microarray as a platform for protein crystal growth. The methods would also utilize automatic dispensing of solutions and scoring of crystal growth.

SUMMARY OF THE INVENTION

The present invention is a method of screening protein crystal growth conditions employing a minimal amount of protein, preferably on a picogram to microgram scale. Each screening sample has picogram to microgram amounts of protein in a picoliter to nanoliter volume. Predetermined protein crystal growth conditions are maintained and crystal growth is analyzed using both qualitative and quantitative criteria.

In a preferred embodiment, a microarray is provided for use in methods of screening protein crystal growth. Preferably the microarray has a plurality of micro-chambers in the microarray. The micro-chambers may be passive or a combination of passive micro-chambers that are connected with miniaturized active control elements such as, but not limited to, valves, pumps and electrodes. A protein solution is automatically dispensed into the micro-chambers. The protein crystal growth conditions of each of the micro-chambers is adjusted so that the protein crystal growth conditions of at least two of the micro-chambers differs. Protein crystal growth in the micro-chambers is then analyzed based on both the qualitative amount of crystallization and the quality of the crystals formed.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF INVENTION

Figure 1:
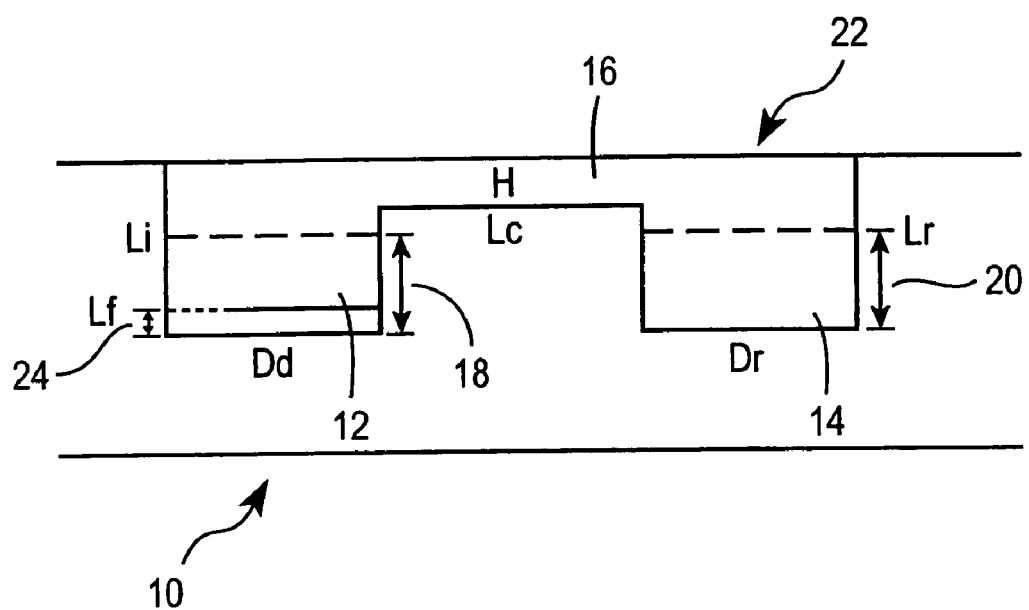
FIG. 1 is a schematic illustrating a two well design in a microarray.

The method of the present invention is for screening protein crystal growth conditions in protein solutions employing a minimal amount of protein in a minimal volume, preferably on a pico, nano or meso scale. Pico, nano or meso scale as used herein preferably employs (on average) picogram (pg), nanogram (ng) or microgram (µg) amounts of protein in picoliter (pl) or nanoliter (nl) volumes. Preferably, the amount of protein in each screening sample is less than about 5 µg. More preferably, the amount of protein in a screening sample will be less than about 1 µg. In one embodiment, the volume of protein solution in a screening sample is preferably from about 0.001 nl to about 250 nl and more preferably about 0.01 nl to about 10 nl. It will be appreciated by those skilled in the art that the volumes actually employed for any particular protein will be a function of (without limitation) the target protein and its concentration in the protein solution.

The protein solution contains one or more desired proteins for crystallization. As used herein, the term "protein" is meant to include all naturally occurring and synthetic peptides, polypeptides, proteins, and protein complexes. In one preferred embodiment the concentration of protein in the solution is from about 0.1 µg/µl to about 50 µg/µl, more preferably from about 0.1 µg/µl to about 10 µg/µl, and still more preferably about 0.1 µg/µl to about 1.0 µg/µl. In another preferred embodiment, the solution is buffered to a pH between about 2.0 and about 10.0, more preferably from about 3.0 to about 8.5. If desired, the protein solution may optionally contain agents that aid in solubilizing the protein at the desired protein concentration or conditions. For example, if the protein is a membrane protein, the protein solution may optionally contain one or more surface active agents, such as a detergent mixture. In one preferred embodiment, the protein solution also comprises components that assist in crystallization. By way of non-limiting example, the protein solution will comprise an aqueous salt solution, polyethylene glycol, or an alcohol. Such components as well as their selection, ranges, contraindications and the like are well known to those skilled in the art. See, for example, Gilliland, G. L. et al., *Acta Crystallogr.* D50: 408–413 (1994); McPherson, A., *Crystallization of Biological Molecules*, Cold Spring Harbor Press, Cold Spring Harbor, N.Y., pp. 487–524 (1999), expressly incorporated by reference.

The protein solution is dispensed onto a platform. The platform can be, by way of non-limiting example, a glass slide, a multi-well plate or a microarray. The solution is preferably dispensed using a device with picoliter or nanoliter accuracy. Preferably the dispensing device has at least a 90% accuracy on a picoliter or nanoliter scale. The protein solution can be dispensed manually using, for example, a syringe. In a highly preferred embodiment, automatic dispensing devices are used to dispense the protein solution.

A second solution, the reservoir or precipitate solution is provided. The precipitate solution is a solution that helps to bring about protein crystallization. It can comprise, for example, a salt solution, an alcohol or a polyethylene glycol. The second solution is provided either before, after, or simultaneously with the protein solution. The volume of the precipitate solution is typically equal to or greater than the volume of protein solution. The placement of the second solution is dependent on the crystallization method used but is typically in fluid communication with the first solution. Fluid communication can be liquid—liquid, liquid-vapor or vapor—vapor communication. Generally, a channel is provided for fluid communication. A channel is broadly defined herein as a space that enables fluid communication to occur. In the liquid—liquid diffusion method, the protein solution and precipitate solution contact each other at an interface. In batch crystallization, the two solutions are mixed together. If vapor diffusion crystallization is desired, the two solutions are kept separate but space is allowed for the diffusion of vapor between the solutions. Or, in an alternate embodiment, a single source or reservoir of the second solution may be employed. In yet another alternate embodiment, a desiccant source or a dry gaseous reservoir may be employed in place of the second solution. Specific conditions and variations in these methods are well known to the skilled artisan.

Protein crystal growth is monitored periodically, either qualitatively, quantitatively, or both. This may be by manual inspection using high resolution microscopy or electron microscopy. Preferably, protein crystal growth may be monitored automatically, by, for example, high resolution optical means which automatically detects crystal growth based on, for example, edge analysis. The microscopy can be differential interference contrast microscopy. If desirable crystal growth is observed in a sample, the protein crystal growth conditions of the sample can be reproduced on a macro scale to produce a protein crystal for further analysis. Alternatively, if a precipitate or a clear sample is observed, these conditions can be used to optimize the conditions for additional screening. It will be appreciated that the platform must employ at least one path that is visually and/or optically clear to the method of detection.

In at least one preferred embodiment the method of the present invention for screening protein crystal growth employs a microarray with a plurality of wells or reservoirs as the platform. A microarray may be constructed, for example, similar to a micro-electromechanical chip. The microarray preferably has a planar shape and employs a size and thickness that are compatible with manual or automated plate grippers. The microarray can be made from different materials and by different techniques known to those skilled in the art. The material of the microarray that includes the wells or reservoirs is preferably minimally water absorbing, and is otherwise sufficiently unreactive with the components of the solution. This may be done as a laminate or provided as a coating, for example. Alternatively, a material that absorbs water at a predictable rate can also be used to construct the wells or reservoirs. The volumes of protein and precipitate solutions may then be adjusted to compensate for the water absorption of the material. Preferred materials include, but are not limited to, glass, fused silicon, quartz, a silicon wafer, a polymer or a polysulphone. Alternatively, the microarray can be made from a material coated with a hydrophobic material, such as polysulphone, to limit water absorption in the microarray. Alternatively, the microarray comprises more than one material. Preferably, the microarray is a composite with a bottom of thin glass plate bonded to plastic, glass, silicon rubber or other materials in which wells can be manufactured, with at least one side providing an optical path that is acceptable to the detection technique employed.

In an alternate embodiment, the surfaces of the wells are hydrophobic. For example, the material of the microarray may have a hydrophobic surface. Alternatively, the surfaces of the wells may be coated with a hydrophobic coating. Although not necessary, the hydrophobic surfaces of the wells prevent the drops of solutions from spreading.

The microarray includes a multitude of micron sized wells on the surface of the chip. The term wells encompasses wells, micro-chambers and any indentation sufficient of holding or retaining a desired volume of from about 0.001 nl to about 500 nl, preferably from about 0.01 nl to about 20 nl. The wells are spaced from each other on the surface. The precise number of wells on the surface of the microarray can vary, and the total number of wells on the surface is a matter of choice for the user.

Each of the wells has a volume sufficient to hold an amount of protein solution adequate for growing a protein crystal. Preferably, each of the wells holds a volume from about 0.001 nl to about 250 nl, preferably from about 0.01 nl to about 10 nl.

The wells of the microarray are made by using an etchant such as hydrogen fluoride or by other known etching or fabrication techniques.

The wells can include known means for controlling conditions, individually or collectively, such as pressure, heating or cooling the wells, humidity levels in the wells as well as known means for stirring materials loaded into the wells.

Figure 2A:
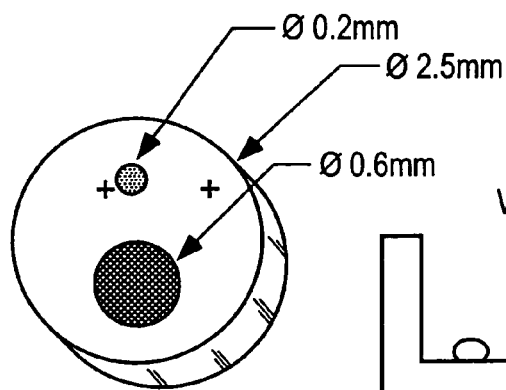
FIG. 2A is a schematic showing a top view of the placement of protein and precipitate solutions in a one well design.
Figure 2B:
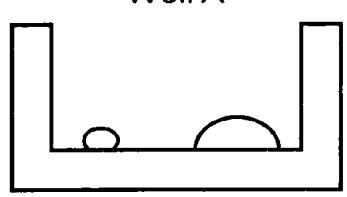
FIG. 2B is a schematic showing a side view of placement of protein and precipitate solutions in a one well design.
Figure 2C:
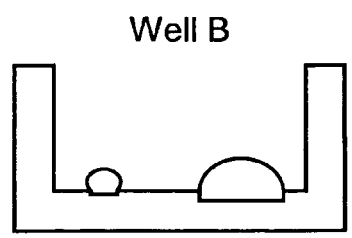
FIG. 2C is a schematic showing a side view of an alternative placement of protein and precipitate solutions in one well.
Figure 2D:
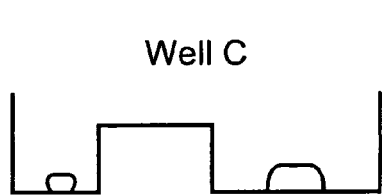
FIG. 2D is a schematic showing a side view of placement of protein and precipitate solutions in two wells.
Figure 2E:
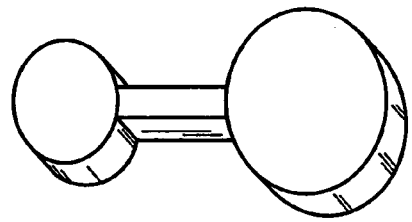
FIG. 2E is a schematic showing a top view of the placement of protein and precipitate solutions in a two well design.

In one arrangement, the wells of the microarray are not connected and separate from each other. In an alternative arrangement, adjacent wells of the microarray are connected by one or more channels which provide fluid communication between the adjacent wells (FIGS. 1 and 2D–E). Preferably, the connecting channels will have cross-section dimensions and length allowing control over the rate of transport of fluid, vapor, buffer, or precipitating or crystallizing agents through the channels. In one embodiment, varying the dimensions of the channels controls protein crystal growth condition. In an alternate embodiment, protein crystal growth conditions are controlled by placing a material in the micro-channels that controls fluid communication between the wells. Non-limiting examples are membranes, acrylamide or agarose. For example, the connecting micro-channels are from about 0.0001 to about 0.2 microns wide and from about 0.00005 to about 0.1 microns deep. Alternatively, the micro-channels are from about 0.0001 to about 2.0 microns wide and from about 0.00005 to about 0.5 microns deep. The micro-channels are formed in the microarray chip by the known etching techniques.

An example of two wells in a microarray (10) connected by a micro-channel is shown in FIG. 1. The protein solution well 12 is connected to precipitate solution well 14 by a microchannel 16. The dimensions of each well are designed to hold the desired amount of solution and may have the same or different dimensions. Initially, protein sample is dispensed into well 12 to an initial liquid height 18 and precipitate solution is dispensed into well 14 with liquid height 20. The top of the wells and microchannel are sealed by an optically clear cover 22. In vapor diffusion crystallization, the precipitate solution in well 14 has a lower vapor pressure than the protein solution in well 12, causing diffusion of solvent from well 12 to well 14 until the solution liquid height in well 12 reaches a final height 24. The concentration of the protein solution in well 12 precipitates protein crystal formation.

The microarray can also include a known means for transmitting a fluid or gas to the wells of the microarray from an external source. For example, an external mechanical pumping system marketed by Watson-Marlowe, Inc., under the trade designation "205U" can be used. The pumping system is a multi-channel cassette which delivers fluid or gas in reproducible and accurately controlled amounts.

Optionally, micro-valves are disposed in the wells and micro-channels to regulate the flow of fluid or vapor between the wells and through the micro-channels in a known manner.

An automated dispensing mechanism capable of accurately and/or repeatedly dispensing picoliter and/or nanoliter volumes is also provided. Preferably, the automated dispensing mechanism has an accuracy of at least about 90%. The automated dispensing mechanisms are preferably Piezo-based or fast solenoid dispensing mechanisms. More preferable, the dispensing mechanism is a fast solenoid dispensing mechanism. The dispenser has a large number of parallel capillaries. The capillaries are in fluid communication with a source of protein solution, a source of precipitate solution, and a source of buffer solution. The dispensing can be actuated by ultrasonic transducers that efficiently produce a pressure wave in the capillaries that contain the solutions. The dispenser is analogous to ink jet printer heads for computer printers but the fluid is not heated, thus not damaging the solutions.

The protein solution preferably comprises an aqueous protein solution at a concentration of from about 0.1 µg/µl to about 50 µg/µl. Preferably, the concentration is from about 0.1 µg/µl to about 10 µg/µl, more preferably from about 0.1 µg/µl to about 1.0 µg/µl. Preferably, the protein solution comprises a detergent mixture when crystallizing membrane proteins. The precipitate solution preferably comprises a concentrated aqueous salt solution or polyethylene glycol as precipitating agents. The buffer solution preferably has pH between about 2 and about 10.

The automated dispensing mechanism dispenses an initial volume of protein solution, an initial volume of precipitate solution, and an initial volume of buffer solution from the source of protein solution, the source of precipitate solution, and the source of buffer solution, respectively, into preselected wells or connecting channels of the microarray.

The placement of the initial volume of protein solution, the initial volume of precipitate solution, and the initial volume of buffer solution in the preselected wells or channels of the microarray is dependent upon the method utilized to effect crystallization of the protein in the protein solution.

Preferred methods to effect crystallization of the protein in the protein solution include liquid—liquid diffusion, batch diffusion, and vapor diffusion.

In the liquid—liquid diffusion method, the initial volume of protein solution is placed in one set of preselected wells, and the initial volume of precipitate solution is placed in a separate or different set of wells. The protein solution wells are connected to the precipitate solution wells by micro-channels. The initial volume of buffer solution may be placed in the micro-channels, or alternatively added directly to the initial volume of protein solution and/or precipitate solution.

The concentration, amounts, precipitate type, and pH of the initial volumes of protein solution, precipitate solution, and buffer solution are primary conditions which determine protein crystal growth in a protein solution. In preparing the initial solutions, and in the automated dispensing mechanism placement, these conditions and the sample placement are varied in accordance with a pre-designed program.

A cover plate is affixed to the microarray to convert the wells to micro-chambers and to convert the micro-channels to a capillary tube structure. The cover plate can made of the same or different material as the microarray, but the cover plate (or some portion of the well or chamber) must be transparent to permit optical analysis of the protein solutions in the chambers of the microarray. Preferably, the cover plate will be glass or other material that is visually or optically clear, such as an optically clear tape.

Alternatively, the environment surrounding the microarray can be controlled to limit evaporation of the solutions. Under controlled conditions of, for example, temperature and humidity, covering the samples may not be necessary.

The crystallizing agent in the precipitate solution, in selected micro-chambers, diffuses via the connecting capillaries to selected micro-chambers containing protein solution.

Protein crystal growth in the different chambers are then monitored by high resolution or other optical means which automatically detects crystal growth based on well known edge analysis. Alternatively, the protein crystal growth can be monitored by manual inspection using high resolution microscopy or electron microscopy. Preferably the protein crystal growth in the chambers is monitored by high resolution optical means which automatically detects crystal growth based on edge analysis.

Once crystal growth in a chamber is detected, that chamber's protein crystal growth conditions can be reproduced on a macro scale to produce a protein crystal which can be analyzed by x-ray crystallography. Alternatively, if a precipitate or clear sample is observed, the conditions in those samples can be used to optimize conditions for additional screening.

In the vapor diffusion method, the initial volume of protein solution is placed in one set of preselected wells, and the initial volume of precipitate solution is placed in a separate or different set of wells based on a pre-designed program, as with the liquid—liquid diffusion method (FIGS. 2D–E). The protein solution wells are connected to the precipitate solution wells by micro-channels. The initial volume of buffer solution is added to the initial volume of protein solution and/or initial volume of precipitate solution. Alternatively, the protein solution and precipitate solution can be placed in the same well such that the two solutions do not come into contact (FIGS. 2A–C).

As with liquid—liquid diffusion, the crystal growth is varied in different wells in accordance with a pre-designed program in which the placement, concentration, amounts, precipitate type, and pH conditions are varied in the different wells.

A cover plate is then affixed to the microarray as with the liquid—liquid diffusion method. The vapor pressure of the precipitate solution is lower than the vapor pressure of the protein solution. This causes the protein solution in a microchamber which is connected via a capillary to a microchamber containing a precipitate solution to evaporate and become super-saturated causing precipitation of protein. Crystal growth is monitored as in the liquid—liquid diffusion.

Alternatively, the protein solution is placed into wells of the microarray and the microarray is exposed to a single reservoir with the precipitate solution. This method allows for less fluid dispensing, but also less control of the protein crystal growth conditions with respect to each protein sample.

To further control protein crystal growth the protein solution and/or precipitate solution can be covered with an oil solution. Preferably, the oil solution is inert and immiscible with respect to the protein and precipitate solutions while allowing for water diffusion through the oil and has a density less than the protein and/or precipitate solution. More preferably, the oil solution contains paraffin oil, silicone oil, or mixtures thereof and most preferably, the oil contains a mixture of paraffin and silicone oils. It will be appreciated by the skilled artisan that other oil mixtures may be used as long as the oils are miscible with each other. See Chayen, N. E., *Structure* 5, 1269–1274 (1977).

Water can evaporate at different rates through different oils. Paraffin oil can act as a good sealant allowing only a negligable amount of water evaporation through it during the average time required for a crystallization experiment. In contrast, water can diffuse readily through silicone oils. A mixture of paraffin and silicone oils permits partial diffusion, with the amount and rate of diffusion controlled by the ratio at which they are mixed. If a mixture of paraffin and silicone oils are used, the ratio of paraffin oil to silicone oil preferably is from about 90:10 vol % to about 10:90 vol %. More preferably, the ratio is from about 90:10 vol % to about 50:50 vol % paraffin oil to silicone oil. It will be appreciated that the preferred ratio of paraffin oil to silicone oil will also depend on whether the wells are further sealed with a coverplate to form discrete microchambers in each well. When a coverplate is used evaporation is limited and a higher ratio of silicone oil may be used. However, when all the wells of the microarray are exposed to a single reservoir of precipitate solution, use of a cover plate may not be feasible and it may be desirable to have a higher proportion of paraffin oil in the oil mixture.

Alternatively, covering the protein and/or precipitate solution with at least two distinct layers of oil can control protein crystal growth. Preferably both oils are inert and immiscible with respect to the protein and/or precipitate solutions and have a density less than the solutions. More preferably the oils have different densities such that they form discrete layers, one on top of the other, covering the protein solution. The oils may be either miscible or immiscible with respect to the oils. It will be appreciated that if the oils are miscible, additional care will be taken addition of the oils to the well. Most preferably, the oils also have different water diffusion properties with respect to each other. By way of non-limiting example, a layer of paraffin oil having a density heavier than silicone oil can be added to a well containing protein solution. A layer of silicone oil is then carefully added on top of the paraffin oil layer. It will be appreciated that crystal growth conditions can be further controlled by adjusting the volume of each oil layer covering the solutions.

Protein crystallization can also be controlled by the thickness of the oil layer, which in practice is controlled by the volume. A larger volume of oil in relation to the volume of the protein and/or precipitate solution will result in slower vapor diffusion. In contrast, the smaller the volume of oil, the vapor diffusion will be more rapid. Preferably the volume of oil in each well is from about 1 ml to about 100 ml and more preferably from about 10 ml to about 80 ml.

In one method of the present invention, the drop of protein or precipitate solution is placed in the well initially and then the oil solution is added to the well. In an alternate method, the oil may be added to the well first and then the protein or precipitate solution is dispensed directly into the oil solution. With either method the protein or precipitate solution, having a density greater than the oil, will be positioned on the bottom of the well.

A further method of the present invention includes "containerless crystallization" in which a drop of protein solution is positioned between two layers of two different oils. The protein solution therefore does not come in contact with the sides of the well. Preferably the two oils are immiscible with respect to each other and the protein solution. More preferably a flat meniscus forms between the two oil layers. The bottom oil will have a higher density than the protein solution while the top oil will have a lower density than the protein solution. Preferably the bottom oil is a high density fluorinated silicone oil and the top oil is a silicone oil. In a preferred method, both oils are added to a well. They can be added simultaneously or sequentially. A drop of protein solution is then added to the well. The drop of protein solution should be positioned between the two oil layers toward the center of the well and not be in contact with the sides of the well. See Chayen, N. E., *Protein Engineering* 9, 927–929 (1996).

In the batch method, the volume of protein solution, the volume of precipitate solution, and the volume of buffer solution are placed together in individual wells of the microarray. In this method, the chip does not have connecting channels between the wells.

As with liquid—liquid diffusion and vapor diffusion methods, the crystal growth is varied in different wells in accordance with a pre-designed program in which the placement, concentration, amounts, precipitate type, and pH conditions are varied in the different wells.

As with liquid—liquid diffusion and vapor diffusion methods, a cover plate is affixed to the microarray, and the crystal growth is then monitored. Additionally, as described for vapor diffusion methods, the protein and precipitate solutions may be immersed in an oil solution.

If desired, fluid or gas can delivered to the micro-chambers in reproducible and accurately controlled amounts from an external source by the external mechanical pumping system described above. Gas can also be delivered from the pressure generated by a standard glass bottle or tank. The fluid or gas delivered to the micro-chambers can be regulated by the micro-valves. The fluid or gas can be used to further alter the crystal growth conditions of the micro-chamber and increase the size of the protein crystals grown. These protein crystals can then be harvested and examined by x-ray crystallography or nuclear magnetic spectroscopy or other appropriate techniques.

Advantages of the present invention should now be apparent. The present invention provides a method of screening protein crystal growth conditions on a nano or meso scale. The method provides a means of screening protein crystal growth conditions for proteins that cannot be expressed in milligram quantities as well as those that can be expressed in larger quantities. Moreover, the substantial reduction in protein needed for the present invention reduces the costs associated with screening protein crystal growth conditions.

Also provided is an apparatus for screening crystal growth conditions. The apparatus comprises a microarray for the protein and precipitate solutions, an automatic dispensing mechanism for dispensing the solutions and an automated means for analyzing crystal growth.

The desired solutions, i.e., protein, precipitate and a buffer, are preferably automatically dispensed at a preset picoliter or nanoliter volume into the microarray by an automated dispensing mechanism. Preferably, the automatic dispensing mechanism dispenses discrete drops. Screening conditions such as the type of buffer and pH can be varied from sample to sample by programming the automatic dispenser. For example, arbitrary screens varying pH could be programmed by mixing the proper ratios using different drop counts from different stock solutions having different pH values. A pH range from 2.0 to 10.0 is then screened in steps of 0.2–0.5 pH units. Other conditions, such as crystallization agents and salt concentration are also controlled in a similar manner.

Mixing of the reagents can either be done before dispensing or after the solutions are dispensed into the microarray. Mixing in the microarray, for example, can be accomplished by ultrasonic mixing, high-speed dispensing of picoliter drops, rapid temperature fluctuation, or by static diffusion.

After mixing, preferably the wells of the microarray are sealed to control the microenvironment in the wells and to prevent evaporation of the solutions to dryness. Preferably the wells are sealed with an oil, a glass cover plate, or an optically clear tape. More preferably, the wells are sealed with optically clear tape and most preferred, the wells are sealed with both oil and either a glass cover plate or optically clear tape. The oil can be added at any time during the dispensing of the solutions. Sealing the microarray involves an arm mounted on a YZ transverse mechanism. The X direction is along the plate transport direction. The arm, holding a roll of clear tape, moves past the last well in the row, drops to form positive vertical (Z axis) pressure, and then begins to move back in the negative Y direction while at the same time rotating the tape roll. Once the tape leaves the plate area, a guillotine mechanism shears the tape. The plate then moves in the X direction onto the next indexed row and the dispense process initializes again. Automated taping is reliably performed in many industries.

Protein crystal growth in the different wells is monitored by high resolution optical means which automatically detects crystal growth based on well known edge analysis. Such image acquisitions systems are commercially available.

The foregoing and other aspects of the invention may be better understood in connection with the following example, which is presented for purpose of illustration and not by way of limitation.

EXAMPLE 1

Figure 3:
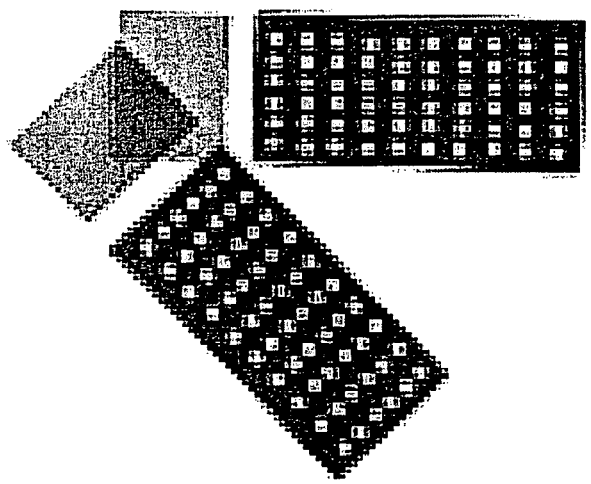
FIG. 3 is a photograph showing a microarray.
Figure 4:
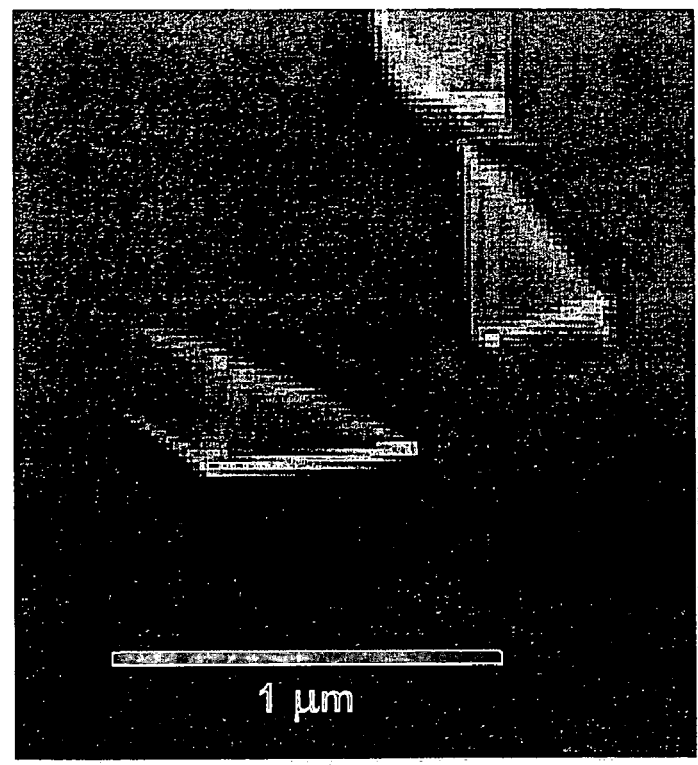
FIG. 4 is a photograph of a protein crystal obtained with nanogram amounts of protein in nanoliter volumes.

Nanoliter protein droplets were used for vapor diffusion, batch and liquid diffusion crystallization screening. The protein solutions of either lysozyme, thaumatin, or NAD synthetase were applied using a five microliter Hamilton syringe. To ensure complete wetting of the small droplet to the experiment chamber, the tip of the Hamilton syringe was placed in contact with the wall of each experiment chamber. A variety of microarrays were designed to accommodate protein solution droplets with volume ranges of 5–20 nanoliters and precipitate volumes of 100–200 nanoliters. The array prototyping was accomplished using MicroScope slides with permanent sealing of neoprene gaskets of varying thickness (0.1 mm 0.5 mm). Once all solutions were applied to an individual experiment chamber within the microscope slide, the experiment was sealed (with oil or grease) by placing a glass cover slide over the top of the gasket. FIG. 3 is a photograph of a typical design for a 60 chamber array prototype (gasket thickness=0.1 mm) and FIG. 4 is a photograph of crystals that were grown to 10 nanoliter protein droplets using a similar microarray slide.

A Cartesian robotic dispensing system was used to prepare crystallization solutions in a 6 by 10 experiment array. Five nanoliters of protein plus five nanoliters of precipitant were dispensed into one merged droplet in one depression in the experiment chamber (FIG. 3) and 50 nanoliters of precipitant plus 50 nanoliters of buffer were merged into one droplet in the connected depression. Thus, four solutions were dispensed for each experiment, and 6×10×4=240 total for the entire 6 by 10 array. Cartesian's instrument was able to dispense all of the solutions in less than 20 minutes. All external conditions used were known crystallization conditions for the particular proteins tested. The experiment was manually sealed and incubated at 22° C. for a period of one day. Crystals were observed in seventy percent of the droplets. While not wishing to be bound by theory, it is believed that the failure to observe crystals in 30% of the wells was due to inaccurate dispensing of the protein and precipitant five nanoliter drops in that the peizo tip did not position the drops together.

From the above description of the invention, those skilled in the art will perceive improvements, changes and modifications. Such improvements, changes and modifications within the skill of the art are intended to be covered by the appended claims.

Having described the invention the following is claimed:

1. A method of screening protein crystal growth conditions comprising:
   dispensing a protein solution into protein solution microchambers of a microarray and separately dispensing precipitate solutions into precipitate solution microchambers of said microarray, said microchambers having a volume from about 0.001 nl to about 250 nl;
   allowing liquid—liquid communication between protein solution microchambers and precipitate solution microchambers; and observing said microchambers for protein crystal growth or protein precipitation.

2. The method of claim 1 wherein said precipitate solution comprises a component selected from the group consisting of buffers, surface active agents, salts, alcohols, polyethylene glycol and mixtures thereof.

3. The method of claim 1 wherein said protein solution is buffered.

4. The method of claim 1 wherein said microarray comprises valves between protein solution microchambers and precipitate solution microchambers.

5. The method of claim 4 wherein said valves control said liquid—liquid communication between microchambers comprising protein solution and microchambers comprising precipitate solution.

6. The method of claim 5 wherein controlling protein crystal growth further comprises employing microchambers of varying dimensions.

7. The method of claim 1 wherein said precipitate solution and said protein solution are in fluid communication via micro-channels.

8. The method of claim 4 wherein said precipitate solution and said protein solution are in fluid communication via a channel.

9. The method of claim 5 wherein said allowing liquid—liquid communication of said precipitate solution microchambers and said protein solution microchambers comprises opening said valves.

10. A method of screening protein crystal growth conditions comprising:
   transferring samples comprising a volume from about 0.001 nl to about 250 nl of a protein solution into microchambers in a platform;
   providing a precipitate solution that is in liquid—liquid communication with the protein solution;
   controlling the protein crystal growth conditions of the samples; and
   observing a protein precipitate or protein crystals in the microchambers.

11. The method of claim 10 wherein controlling the protein crystal growth condition comprises employing a valve disposed in a microchannel between a microchamber comprising protein solution and a microchamber comprising precipitate solution.

12. The method of claim 10 therein the platform is a microarray.

13. The method of claim 1, wherein the volume of the protein solution microchambers is between about 1 to about 10 nanoliters.

14. The method of claim 1, wherein the volume of precipitate solution microchambers is between about 1 to about 10 nanoliters.

15. The method of claim 1 wherein said microarray comprises miniaturized active control elements between protein solution microchambers and precipitate solution microchambers.

16. The method of claim 15 wherein the miniaturized active control elements are selected from the group consisting of valves, pumps, and electrodes.

* * * * *